(12) United States Patent
Adams et al.

(10) Patent No.: US 11,904,133 B2
(45) Date of Patent: Feb. 20, 2024

(54) INFUSION PUMP SYSTEMS AND METHODS FOR ADMINISTRATION SETS

(71) Applicant: Smiths Medical ASD, Inc., Plymouth, MN (US)

(72) Inventors: Grant A. Adams, Anoka, MN (US); James B. Drost, Woodbury, MN (US); Christopher A. Lacy, Arden Hills, MN (US); Jonathan Sanborn, Saint Louis Park, MN (US); Daniel L. Adamson, Blaine, MN (US); Sameer Pai, Plmouth, MN (US); Steven Plager, Eden Prairie, MN (US); Kevin Krautbauer, Saint Paul, MN (US); Erik Jagger, Deephaven, MN (US); Benn Horrisberger, Blaine, MN (US); Larry R. Zalesky, Shoreview, MN (US)

(73) Assignee: Smiths Medical ASD, Inc., Plymouth, MN (US)

(*) Notice: Subject to any disclaimer, the term of this patent is extended or adjusted under 35 U.S.C. 154(b) by 553 days.

(21) Appl. No.: 15/733,222

(22) PCT Filed: Dec. 14, 2018

(86) PCT No.: PCT/US2018/065685
§ 371 (c)(1),
(2) Date: Jun. 11, 2020

(87) PCT Pub. No.: WO2019/125941
PCT Pub. Date: Jun. 27, 2019

(65) Prior Publication Data
US 2021/0369954 A1    Dec. 2, 2021

Related U.S. Application Data

(60) Provisional application No. 62/607,436, filed on Dec. 19, 2017.

(51) Int. Cl.
*A61M 5/142* (2006.01)
*A61M 5/168* (2006.01)
(Continued)

(52) U.S. Cl.
CPC .... *A61M 5/14228* (2013.01); *A61M 5/16804* (2013.01); *A61M 5/16877* (2013.01);
(Continued)

(58) Field of Classification Search
CPC ............ A61M 5/14228; A61M 60/279; A61M 60/284; A61M 39/28; A61M 39/281;
(Continued)

(56) References Cited

U.S. PATENT DOCUMENTS 3,778,195 A    12/1973    Bamberg
4,236,880 A    12/1980    Archibald
(Continued)

FOREIGN PATENT DOCUMENTS

CN    103702698 A    4/2014
CN    104056322 A    9/2014
(Continued)

OTHER PUBLICATIONS

Smiths Medical, "Graseby 1200 Infusion pump brochure," 2016, downloaded from https://www.shrijihealthcare.com/medical%20equipment/pdf/Smiths%20Graseby%20TM1200.pdf, 4 pages.
(Continued)

*Primary Examiner* — Nilay J Shah
(74) *Attorney, Agent, or Firm* — Husch Blackwell

(57) ABSTRACT

An LVP that provides peristaltic pumping to removably couplable administration set tubing assemblies supplying medical infusate. The LVP includes a housing, a drive-train assembly, and a controller. The housing includes an assembly receptacle configured to receive an administration set tubing assembly. The drive-train assembly provides
(Continued)

mechanical peristaltic movement within the assembly receptacle. The drive-train assembly includes a stepper motor located within the housing and a camshaft assembly, driven by the stepper motor and at least partially extending into the assembly receptacle. The camshaft assembly includes a unitary camshaft and a plurality of tube engaging members that cooperatively move according to rotation of the unitary camshaft. Further, the controller is located within the housing that controls operation of the stepper motor and the camshaft assembly.

21 Claims, 11 Drawing Sheets

(51) Int. Cl.
  *A61M 5/172* (2006.01)
  *A61M 39/28* (2006.01)
  *F04B 43/12* (2006.01)
(52) U.S. Cl.
  CPC ........... *A61M 5/172* (2013.01); *A61M 39/281* (2013.01); *A61M 2205/3334* (2013.01); *A61M 2205/3351* (2013.01); *A61M 2205/3355* (2013.01); *A61M 2205/3365* (2013.01); *A61M 2205/505* (2013.01); *F04B 43/1223* (2013.01)
(58) Field of Classification Search
  CPC ........... A61M 39/284; A61M 5/16804; A61M 2205/505; A61M 5/16877; A61M 2205/3334; A61M 60/00; A61M 60/268; F04B 43/1223; F04B 43/12; F04B 43/08; F04B 43/082
  See application file for complete search history.

(56) References Cited

U.S. PATENT DOCUMENTS

| | | | |
|---|---|---|---|
| 4,277,226 A | | 7/1981 | Archibald |
| 4,302,164 A | * | 11/1981 | Manella ............ A61M 5/14228 417/474 |
| 4,373,525 A | * | 2/1983 | Kobayashi ........ A61M 5/14228 417/474 |
| 4,493,706 A | * | 1/1985 | Borsanyi ........... A61M 5/14228 417/474 |
| 4,561,830 A | | 12/1985 | Bradley |
| 4,617,014 A | * | 10/1986 | Cannon ............. A61M 5/16854 604/246 |
| 4,648,812 A | * | 3/1987 | Kobayashi ............ F04B 43/082 417/474 |
| 4,756,706 A | * | 7/1988 | Kerns .................... A61M 5/142 128/DIG. 13 |
| 4,954,046 A | * | 9/1990 | Irvin ................. A61M 5/14228 417/474 |
| 5,242,279 A | * | 9/1993 | Knuth ................. F04B 43/0072 417/474 |
| 5,368,562 A | | 11/1994 | Blomquist et al. |
| 5,429,485 A | | 7/1995 | Dodge |
| 5,478,211 A | | 12/1995 | Dominiak et al. |
| 5,482,446 A | | 1/1996 | Williamson et al. |
| 5,513,957 A | | 5/1996 | O'Leary |
| 5,534,691 A | | 7/1996 | Holdaway et al. |
| 5,709,534 A | | 1/1998 | O'Leary |
| 5,716,194 A | | 2/1998 | Butterfield et al. |
| 5,741,121 A | | 4/1998 | O'Leary |
| 6,016,044 A | | 1/2000 | Holdaway |
| 6,106,498 A | | 8/2000 | Friedli et al. |
| 6,193,480 B1 | | 2/2001 | Butterfield |
| 6,211,642 B1 | | 4/2001 | Holdaway |
| 6,267,559 B1 | | 7/2001 | Mossman et al. |
| 6,371,732 B1 | | 4/2002 | Moubayed et al. |
| 6,394,771 B2 | | 5/2002 | Butterfield |
| 6,558,347 B1 | | 5/2003 | Jhuboo et al. |
| 6,629,955 B2 | | 10/2003 | Morris et al. |
| 6,731,216 B2 | | 5/2004 | Ho et al. |
| 7,905,710 B2 | | 3/2011 | Wang et al. |
| 8,029,253 B2 | | 10/2011 | Rotem et al. |
| 8,075,514 B2 | | 12/2011 | Butterfield et al. |
| 8,118,778 B2 | | 2/2012 | Haylor et al. |
| 8,337,168 B2 | | 12/2012 | Rotem et al. |
| 8,371,832 B2 | | 2/2013 | Rotem et al. |
| 8,491,284 B2 | | 7/2013 | Miyazaki et al. |
| 8,500,694 B2 | | 8/2013 | Susi |
| 8,535,025 B2 | | 9/2013 | Rotem et al. |
| 8,678,793 B2 | | 3/2014 | Goldor et al. |
| 8,752,436 B2 | | 6/2014 | Beck et al. |
| 8,920,144 B2 | | 12/2014 | Rotem et al. |
| 8,986,252 B2 | | 3/2015 | Cummings et al. |
| 9,163,623 B2 | | 10/2015 | Butterfield et al. |
| 9,238,101 B2 | | 1/2016 | Hariharesan et al. |
| 9,616,170 B2 | | 4/2017 | Nakanishi et al. |
| 9,662,437 B2 | | 5/2017 | Moosai |
| D801,519 S | | 10/2017 | Sabin et al. |
| D812,218 S | | 3/2018 | Lacy et al. |
| D830,546 S | | 10/2018 | Lacy et al. |
| D871,572 S | | 12/2019 | Lacy et al. |
| 2003/0214412 A1 | | 11/2003 | Ho et al. |
| 2006/0184121 A1 | | 8/2006 | Brockman et al. |
| 2009/0076461 A1 | | 3/2009 | Susi et al. |
| 2009/0221964 A1 | * | 9/2009 | Rotem .............. A61M 5/16813 604/151 |
| 2010/0080720 A1 | | 4/2010 | Miyazaki et al. |
| 2012/0136305 A1 | * | 5/2012 | Gagliardoni ........ A61M 39/284 604/151 |
| 2012/0195769 A1 | | 8/2012 | Susi |
| 2012/0257986 A1 | | 10/2012 | Momeni |
| 2013/0149172 A1 | * | 6/2013 | Butterfield .......... F04B 43/1223 417/474 |
| 2014/0100526 A1 | * | 4/2014 | Ueda ....................... F04B 49/10 604/151 |
| 2014/0358111 A1 | | 12/2014 | Brewer et al. |
| 2015/0018766 A1 | * | 1/2015 | Nakanishi ........... A61M 39/281 604/151 |

FOREIGN PATENT DOCUMENTS

| | | |
|---|---|---|
| CN | 205371780 U | 7/2016 |
| EP | 2883559 B1 | 6/2017 |
| EP | 2700424 B1 | 1/2018 |
| JP | H11137682 A | 5/1999 |
| JP | 3133453 | 7/2007 |
| JP | 2013006021 A | 1/2013 |
| JP | 5805415 B2 | 11/2015 |
| JP | 5897815 B2 | 3/2016 |
| WO | WO2005/037349 A2 | 4/2005 |
| WO | WO 2014/113324 | 7/2014 |
| WO | WO 2017/218927 A1 | 12/2017 |
| WO | WO-2019018658 A2 | 1/2019 |

OTHER PUBLICATIONS

Smiths Medical, "Graseby 1200 Large Volume Infusion Pump Quick Reference Guide," 2017, downloaded from https://www.smiths-medical.com/-/media/M/Smiths-medical_com/Files/Import-Files/IN193909GB-052017.pdf, 6 Pages.

International Search Report and Written Opinion from PCT Application PCT/US2018/065685 dated Jul. 2, 2020, 9 pgs.

International Preliminary Report on Patentability from PCT Application PCT/US2018/065685 dated Jul. 2, 2020, 9 pgs.

International Search Report and Written Opinion for International Application No. PCT/US2018/065685 dated Mar. 25, 2019.

* cited by examiner

INFUSION PUMP SYSTEMS AND METHODS FOR ADMINISTRATION SETS

CROSS REFERENCE TO RELATED APPLICATIONS

The present application claims priority to U.S. Provisional Patent Application No. 62/607,436, filed on 19 Dec. 2017, which is hereby fully incorporated herein by reference.

TECHNICAL FIELD

This disclosure relates to infusion pump systems, and more particularly, to large volume pumps (LVPs) and systems and methods for infusion pump administration sets.

BACKGROUND

Various types of infusion pumps have been useful for managing the delivery and dispensation of a prescribed amount or dose of a drug, fluid, fluid-like substance, or medicament (hereinafter, collectively, an "infusate") to patients. Infusion pumps provide significant advantages over manual administration by accurately delivering infusates over an extended period of time. Infusion pumps are particularly useful for treating diseases and disorders that require regular pharmacological intervention, including cancer, diabetes, and vascular, neurological, and metabolic disorders. They also enhance the ability of healthcare providers to deliver anesthesia and manage pain. Infusion pumps are used in various settings, including hospitals, nursing homes, and other short-term and long-term medical facilities, as well as in residential care settings. There are many types of infusion pumps, including ambulatory, large volume, patient-controlled analgesia (PCA), elastomeric, syringe, enteral, and insulin pumps. Infusion pumps can be used to administer medication through various delivery methods, including intravenously, intraperitoneally, intra-arterially, intradermally, subcutaneously, in close proximity to nerves, and into an intraoperative site, epidural space or subarachnoid space.

In a particular type of infusion pump system that is commonly referred to as a "peristaltic" pump system, delivery of an infusate to a patient is typically accomplished with the use of an infusion administration set, that is typically disposable after use and can provide a fluidic pathway (e.g., tubing) for the infusate from a reservoir (such as an intravenous or "IV" bag) to a patient, in cooperation with a pump that controls a rate of flow of the infusate. Peristaltic infusion pumps typically incorporate a peristaltic pumping mechanism that can function by repetitively and temporarily occluding successive sections of tubing of the administration set in a wave-like motion.

A "large volume pump" or "LVP" system is a common peristaltic pump with related components as aforedescribed. In some publications, the term "volumetric pump" may also be variously used to refer to a peristaltic pump or a large volume pump. While various LVPs have been used in medical environments for years, these devices and their associated peristaltic drive components may have limitations to their efficient, effective and safe usage.

Accordingly, there is a desire for improved infusion pumps and systems utilizing administration sets that are advantageous to caregivers and patients and increase safety.

SUMMARY

Embodiments described or otherwise contemplated herein substantially provide the advantages of improving flexibility, ease of use, operation, as well as patient safety, among other advantages, to infusion pumps and systems and methods for infusion pump administration sets.

One embodiment relates to an LVP that provides peristaltic pumping to removably couplable administration set tubing assemblies supplying medical infusate. The LVP includes a housing, a drive-train assembly, and a controller. The housing includes an assembly receptacle configured to receive an administration set tubing assembly. The drive-train assembly provides mechanical peristaltic movement within the assembly receptacle. The drive-train assembly includes a stepper motor located within the housing and a camshaft assembly, driven by the stepper motor and partially extending into the assembly receptacle. The camshaft assembly includes a unitary camshaft and a plurality of tube engaging members that cooperatively move according to rotation of the unitary camshaft. Further, the controller is located within the housing that controls operation of the stepper motor and the camshaft assembly.

In an embodiment, the camshaft has uniformly distributed lobes around its circumference.

In an embodiment, the plurality of tube-engaging members are of identical shape.

In an embodiment, the plurality of tube-engaging members each have engagement ends shaped for tube contact, including a central rounded protrusion as well as secondary rounded features on either side of the central rounded protrusion. In an embodiment, the central rounded protrusion is dimensioned to protrude further than the secondary rounded features but less than an amount necessary to fully occlude the tubing assembly without some contact of the tubing being made by the secondary rounded features.

In an embodiment, the plurality of tube-engaging members include twelve tube-engaging members.

In an embodiment of the LVP, other than portions extending into the assembly receptacle, the plurality of tube-engaging members are surrounded by a second internal housing within the housing.

In an embodiment, a suspended rigid pressure plate for tube compression is located on a receptacle door that is hinged adjacent the assembly receptacle.

In an embodiment, the assembly receptacle includes a set of horizontally-disposed guide rails located above and below the tube-engaging members to prevent vertical tube walk and including three projection features to define planar contact with a suspended pressure plate.

In an embodiment, the controller controls the stepper motor to provide fluid constancy to infusate delivery.

In an embodiment, the housing of the LVP includes tube guides of C-shaped tubing capture structure at the periphery of the housing for retaining tubing of a coupled administration set beyond either side of the assembly receptacle.

In an embodiment, an administration set is removably couplable to the assembly receptacle under an insertion pressure of fifteen Newtons or less.

One embodiment relates to a peristaltic infusion pump drive-train assembly including a stepper motor located within the housing and a camshaft assembly, driven by the stepper motor and partially extending into the assembly receptacle. The camshaft assembly includes a unitary camshaft; and a plurality of tube engaging members that cooperatively move according to rotation of the unitary camshaft.

In an embodiment, the administration set tubing assembly includes a peristaltic tube, a first and second tube coupler, a frame, and a free-flow protection arm. The peristaltic tube is suitable for compression by the drive-train assembly. The first tube coupler and the second tube coupler are each attached at opposing ends of the peristaltic tube and each have a lumen in fluidic communication with the peristaltic tube. The frame is coupled to the first tube coupler and the second tube coupler at spaced-apart locations. The frame is configured for releasable attachment to the LVP in which the peristaltic tube is positioned for engagement with the plurality of tube engaging members. The frame further includes a latching receiver projecting from the frame having a finger press surface. The free-flow prevention arm is hingedly coupled to the frame and has a latching structure sized to cooperate with the latching receiver.

One embodiment relates to a peristaltic infusion pump drive-train assembly including a stepper motor and a camshaft assembly. The stepper motor is sized for operation within an infusion pump housing. The camshaft assembly is driven by the stepper motor and includes a unitary camshaft and a plurality of tube engaging members of identical shape that cooperatively move according to rotation of the unitary camshaft. The camshaft assembly is largely surrounded by a powerbox housing that is sealed behind the plurality of tube engaging members and is limited to openings oriented to the front of the plurality of tube engaging members. The plurality of tube-engaging members each include shaft wear plates and a plurality of blocks at upper and lower locations that protrude from each side of the plurality of tube engaging members to aid in spacing and prevent wear between adjacent tube engaging members.

One embodiment relates to a large volume pump (LVP) system that provides peristaltic pumping to supply medical infusate. The LVP pump system includes: a housing including an assembly receptacle, a drive-train assembly; a controller, and an administration set tubing assembly. The drive-train assembly provides mechanical peristaltic movement within the assembly receptacle, including a stepper motor located within the housing and a camshaft assembly, driven by the stepper motor and at least partially extending into the assembly receptacle. The camshaft assembly includes a unitary camshaft and a plurality of tube engaging members that cooperatively move according to rotation of the unitary camshaft. The controller is located within the housing that controls operation of the stepper motor and the camshaft assembly. The administration set tubing assembly is removably couplable with the assembly receptacle and includes: a peristaltic tube suitable for compression by the drive-train assembly; a first tube coupler and a second tube coupler, each attached at opposing ends of the peristaltic tube and each having a lumen in fluidic communication with the peristaltic tube; and a frame coupled to the first tube coupler and the second tube coupler at spaced-apart locations, the frame configured for releasable attachment to the assembly receptacle in which the peristaltic tube is positioned for engagement with the plurality of tube engaging members.

The above summary is not intended to describe each illustrated embodiment or every implementation of the subject matter hereof. The figures and the detailed description that follow more particularly exemplify various embodiments.

BRIEF DESCRIPTION OF THE FIGURES

Subject matter hereof may be more completely understood in consideration of the following detailed description of various embodiments in connection with the accompanying figures, in which.

Figure 1:
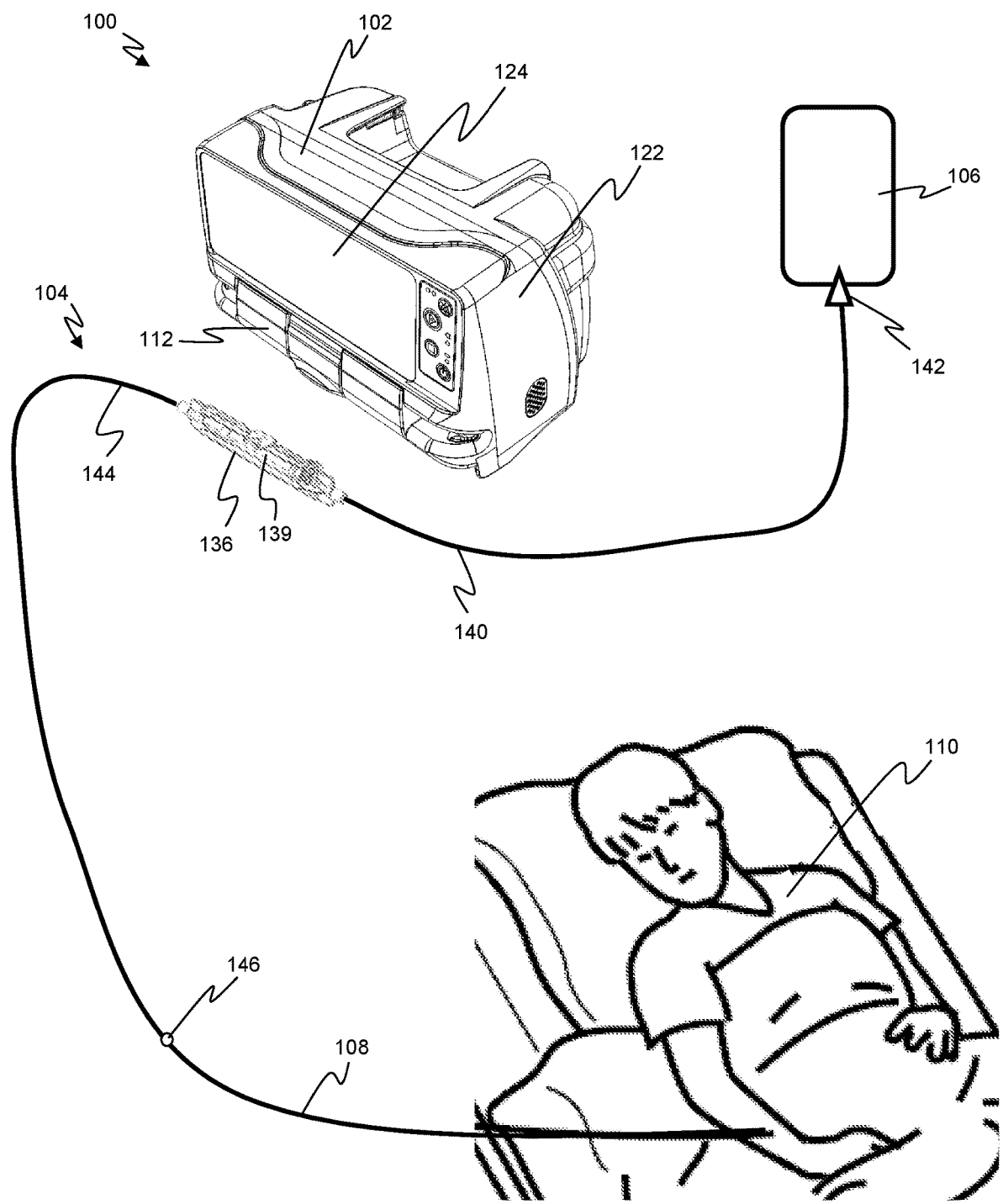
FIG. 1 is a schematic view of an example embodiment of an infusion pump system that includes a LVP and administration set, according to an embodiment.

While various embodiments are amenable to various modifications and alternative forms, specifics thereof have been shown by way of example in the drawings and will be described in detail. It should be understood, however, that the intention is not to limit the claimed subject matter to particular embodiments described. On the contrary, the intention is to cover all modifications, equivalents, and alternatives falling within the spirit and scope of the subject matter as defined by the claims.

DETAILED DESCRIPTION OF THE DRAWINGS

FIG. 1 is a schematic perspective view of an example embodiment of a peristaltic infusion pump system 100 that includes a peristaltic pump 102 (more specifically, an LVP pump 102) and a disposable administration set 104 that is structured and configured to operatively and removably couple to pump 102. Administration set 104 is shown providing a fluidic pathway from an IV bag 106 to an infusion set 108 that ultimately delivers infusate(s) to a patient 110. In FIG. 1, the receptacle door 112 of the peristaltic pump 102 is shown in a closed configuration and administration set 104 is illustrated as not coupled to pump 102.

Figure 2A:
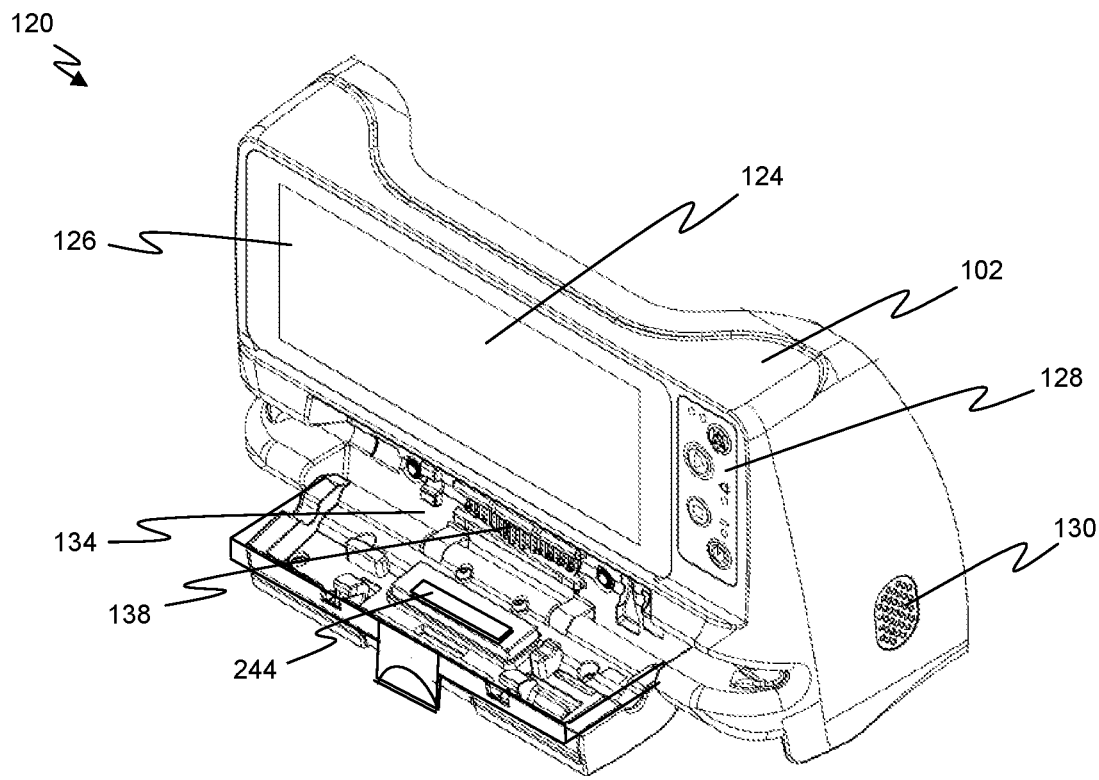
FIG. 2A is a front perspective view of the front assembly of a partial LVP, according to an embodiment.
Figure 2B:
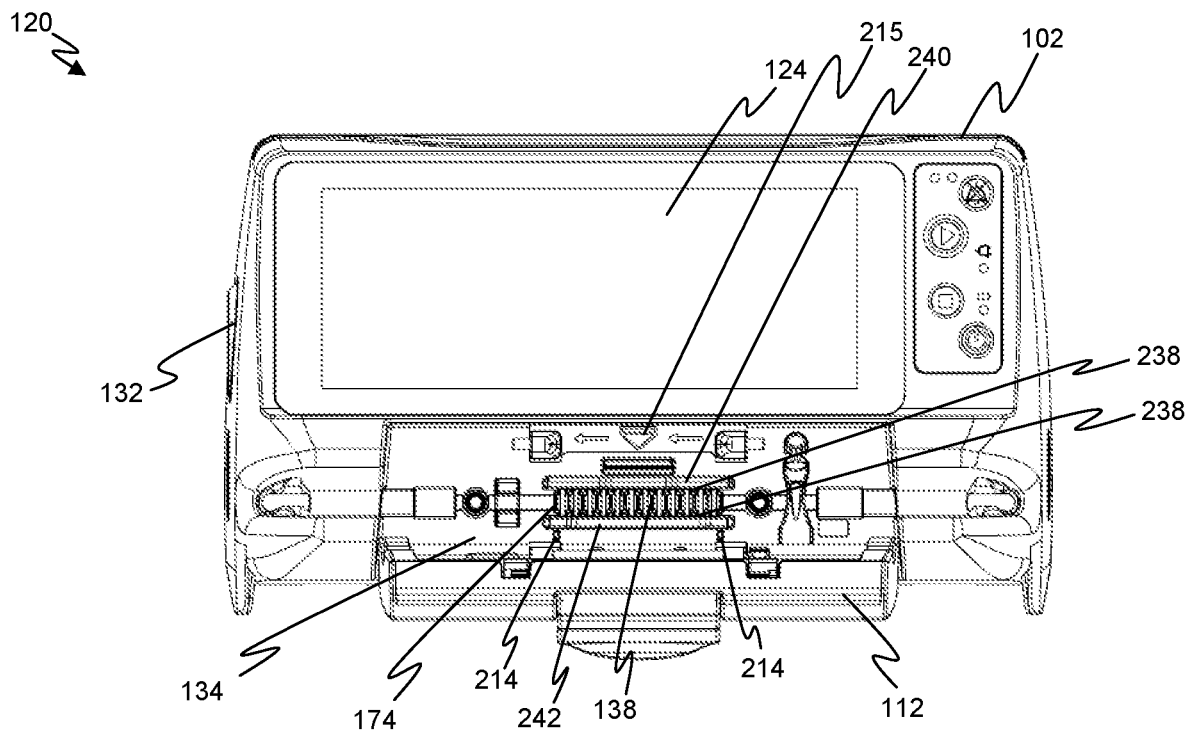
FIG. 2B is a front view of the front assembly of a partial LVP, according to an embodiment.
Figure 2C:
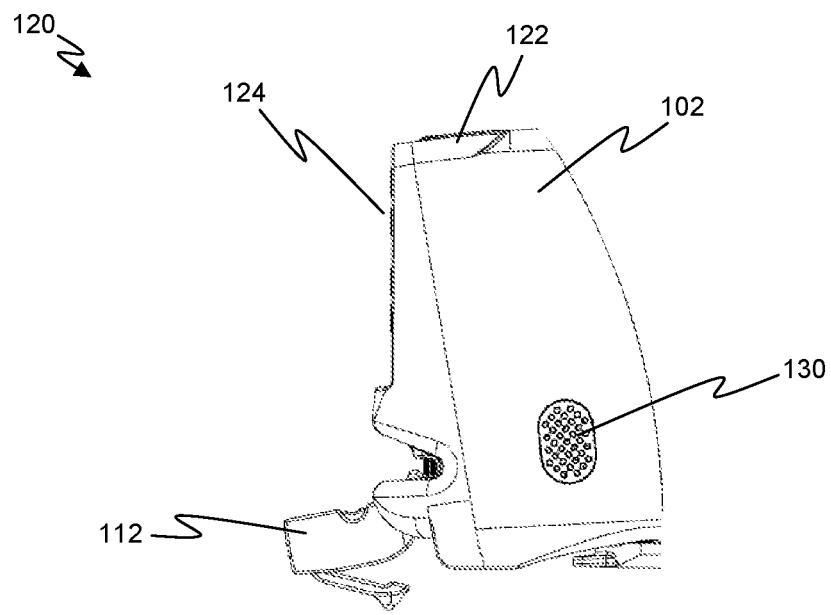
FIG. 2C is a side view of the front assembly of a partial LVP, according to an embodiment.

To more fully illustrate various components of the pump 102, FIGS. 2A-E show a partial depiction of pump 102. Specifically, only the front assembly portion 120 is shown. FIGS. 2A-C depict the front assembly portion 120 of the pump 102 from perspective, front and side views, respectively, where the receptacle door 112 is shown in the open position. The rear portion of the pump 102 is omitted for clarity of view.

With reference to FIGS. 1 and 2A-C, pump 102 includes a housing 122 and a user interface 124 (that can include, for example, a display screen 126, keypad 128, audio speaker 130, and any other suitable user interface components) for prompting and/or relaying commands to a control system or controller of pump 102, and/or for communicating from/to the controller to/from users. User interface 124 generally can allow a user to enter various parameters, including but not limited to names, drug information, limits, delivery shapes, information relating to hospital facilities, as well as various user-specific parameters (e.g., patient age and/or weight) along with so-called "five rights" verification or inputs. Pump 102 can include any appropriate wired or wireless input/output (I/O) interface port 132 and/or protocol (including, but not limited to, USB, Ethernet, WiFi, NFC, Bluetooth, ZigBee, IrDA, and the like) for connecting pump 102 to a network or computer (not illustrated) having software designed to interface with pump 102.

User inputs to pump 102 can be provided by programming from an authorized user, such as a patient, pharmacist, scientist, drug program designer, medical engineer, nurse, physician, or other authorized medical practitioner or healthcare provider. User inputs may utilize direct interfacing (via, e.g., keyboards, touch screens, or other touch-based inputs) as shown, and/or user inputs may utilize indirect or "touchless" interfacing (i.e., gestures; voice commands; facial movements or expressions; finger, hand, head, body and arm movements; or other inputs that do not require physical contact such as cameras, sensors of electric field, capacitance, or sound). User inputs generally can be interfaced, communicated, sensed, and/or received by operator input mechanisms of user interface 124.

As shown in FIGS. 2A and 2B, pump 102 can include an assembly receptacle 134 configured to receive an assembly 136 of the administration set 104 (also, alternatively referred to as an "administration set tubing assembly 136" at times in this document), and a receptacle door 112 that can open and close to allow or block access to assembly receptacle 134. Tube-engaging members 138 of a linear peristaltic pump drive can be located in assembly receptacle 134. Assembly 136 of administration set 104 can be configured and structured to position elements of administration set 104, including a centrally-located segment of tube 139 of assembly 136, in an operative relationship with the linear peristaltic pump drive, including tube-engaging members 138.

Administration set 104 can provide a fluidic pathway from an IV bag 106 or other infusate reservoir to an infusion set 108 that ultimately delivers infusate(s) to a patient 110. It is to be appreciated and understood that, although the present disclosure refers to an IV bag 106 or other infusate reservoir and an administration set 104, subject matter hereof could include or be applicable to a plurality of same, similar, or different infusate reservoirs, infusates, and administration sets. Administration set 104 can include, in addition to assembly 136, upstream tubing 140 that can extend from IV bag 106 or other reservoir to assembly 136. Upstream tubing 140 can terminate in a bag spike 142 or other connector. Administration set 104 can also include downstream tubing 144 that can extend from assembly 136 to infusion set 108. Downstream tubing 130 can be fluidically coupled to infusion set 108 or other catheter with connector 146 such as a Luer-type connector or any other suitable connector, such as one of those contemplated, specified, defined, or described by one of the ISO 80369 series of small bore connector standards.

Figure 2D:
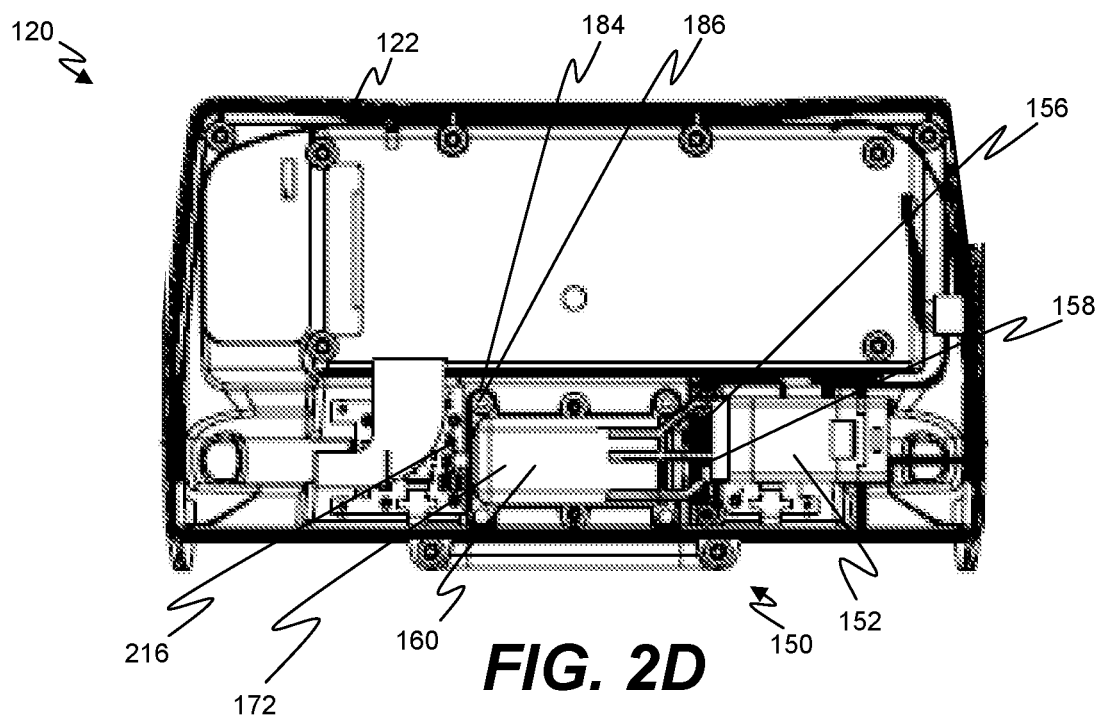
FIG. 2D is a rear view of the front assembly of a partial LVP, according to an embodiment.
Figure 2E:
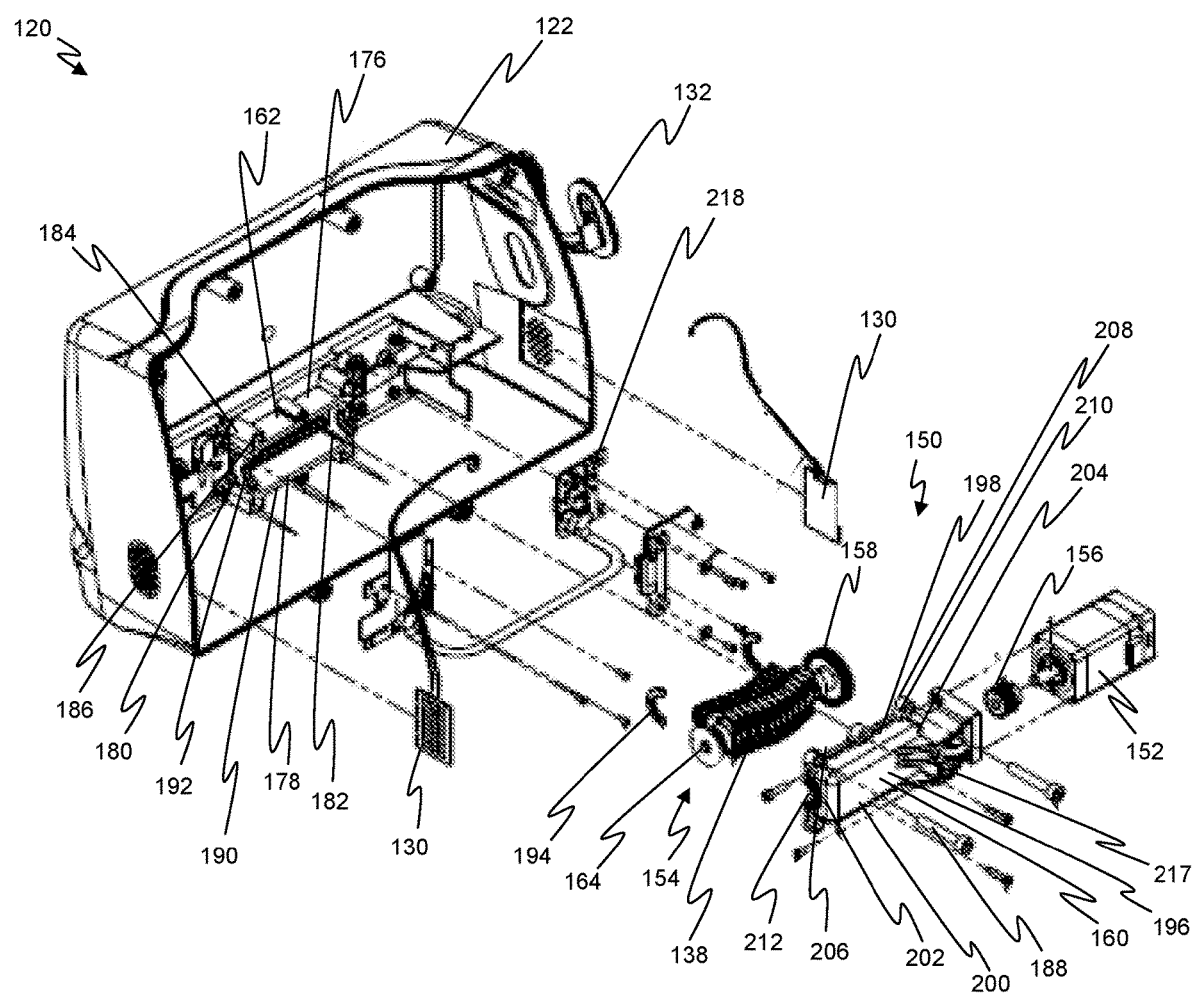
FIG. 2E is a rear perspective exploded view of the front assembly of a partial LVP, according to an embodiment.

FIGS. 2D and 2E, respectively, show an assembled rear view and a rear perspective exploded view of a front assembly portion 120 of pump 102. From these views, the components and features of the peristaltic pump drive or "drive-train" assembly 150 and associated internal portions of the pump 102 can be understood. The drive-train 150 of the pump 102 generally can refer to the motor 152, camshaft assembly 154, and related gears and housing components. Examples of these gears and housing components can include a helical motor gear 156, a helical cam gear 158, a rear powerbox housing 160 and a front powerbox housing 162.

Figure 4:
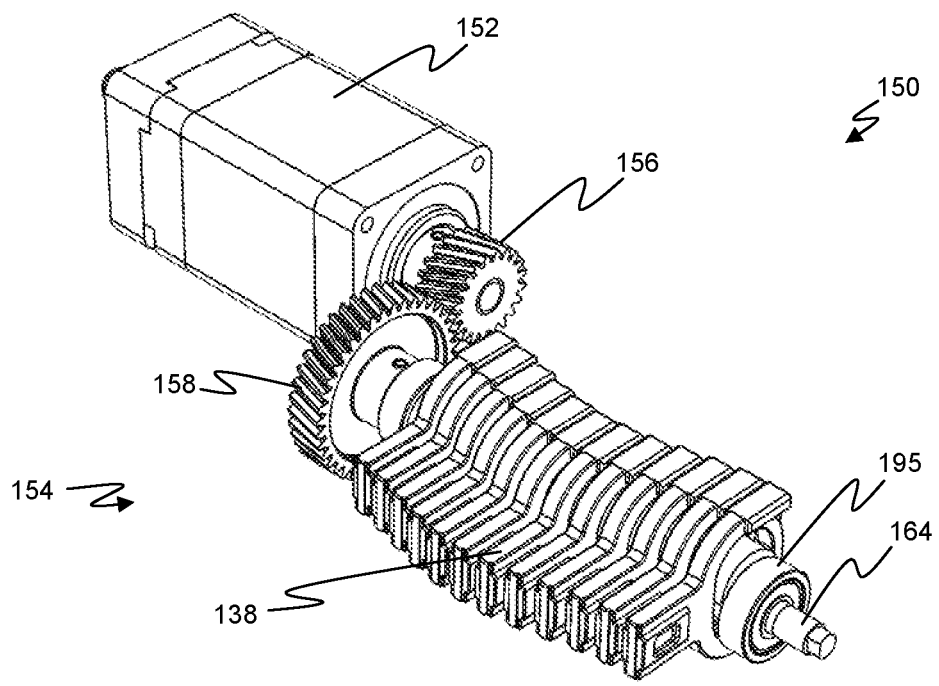
FIG. 4 is a perspective view of an isolated partial drive-train assembly of an LVP, according to an embodiment.
Figure 5:
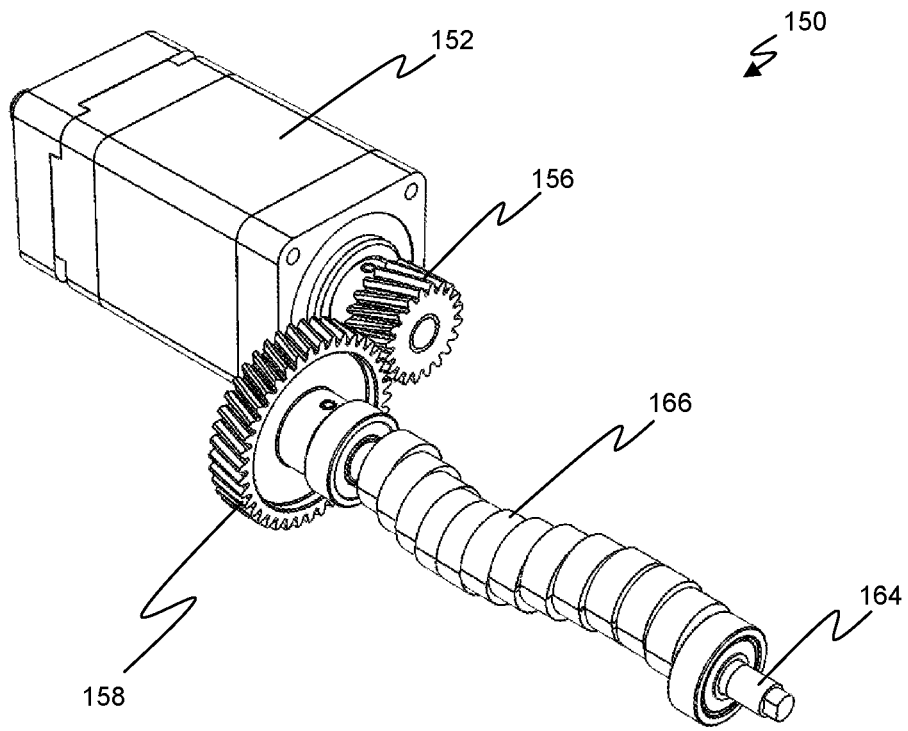
FIG. 5 is a perspective view of an isolated partial drive-train assembly of an LVP, according to an embodiment.

Camshaft assembly 154 includes a unitary camshaft 164 that includes a varying profile of integral, similar, segmented cam portions 166 (see FIG. 5). Surrounding the camshaft 164 are a plurality of tube-engaging members 138 that cooperatively move according to the rotation of the camshaft 164. Specifically, the tube-engaging members 138 each contain an internally defined aperture 168 through which the camshaft 164 passes. Interaction of the camshaft 164 with an interior perimeter surface 170 of the internally defined aperture 168 governs movement of the tube-engaging member 138. See FIGS. 3-9 for more details on the camshaft assembly 154 and its movement.

As shown in FIGS. 2D and 2E, camshaft assembly 154 primarily resides within an internal housing within the larger housing 122 of the peristaltic pump 102. The internal housing is referred to as a power box 172 and is made up of a rear powerbox housing 160 and a front powerbox housing 162. Front powerbox housing 162 projects inwardly into the pump housing 122 and is integrally formed with the pump housing 122. Specifically, inwardly projecting walls of the front powerbox housing 162 internally surround a front central portion of the front housing 122 that includes a central, opening 174 (See FIG. 2B) through which the ends of the tube-engaging members 138 extend when assembled. The inwardly projecting walls include a top wall 176, bottom wall 178, and a pair of side walls 180 and 182. The top wall 176 and bottom wall 178 each include a plurality of spaced-apart structures 184 with apertures 186 for receiving screws or other fasteners 188, spaced around the perimeter of the walls. The most inwardly projecting edge of the walls 176 and 178 provides flat surfaces 190 for interfacing with the rear powerbox housing 160 and/or an intermediate sealing structure between the front powerbox housing 162 and the rear powerbox housing 160. Side walls 180 and 182 each define a curved slot 192 for holding a semi-circular seal 194. These semi-circular seals 194 provide a watertight fit between rotating camshaft support bearings 195 of the camshaft 164 and the front powerbox housing 162.

The rear powerbox housing 160 provides a second half of the powerbox housing 172 to further define an interior cavity and generally complete a structure largely surrounding the camshaft assembly 154. Rear powerbox housing 160 includes rear wall 196, top wall 198, bottom wall 200 and side walls 202 and 204. The top and bottom walls 198 and 200 of the rear powerbox housing 160 extend forwardly from the rear wall 196 to a flat surface 206 for interfacing with the flat surfaces 190 of front powerbox housing 162 and/or an intermediate seal. The top wall 198 and bottom wall 200 each include a plurality of spaced-apart structures 208 with apertures 210 for receiving screws or other fasteners 188, spaced around the perimeter of the walls. Side walls 202 and 204 each define a curved slot 212 for holding a semi-circular seal 194 (not specifically shown in FIG. 2E). These semi-circular seals provide a watertight fit between rotating camshaft support bearings 195 of the camshaft 164 and the rear powerbox housing 160. More specifically, the side walls 202 and 204 of the rear powerbox housing 160 contain bearing locating surfaces for camshaft support bearings 195 found near the respective ends of the camshaft 164.

Accordingly, when assembled, the powerbox housing 172 provides a separate interior housing within the larger overall housing 122 of the pump 102. Other than portions of the tube-engaging member 138 extending into the assembly receptacle 134 via opening 174, the tube-engaging members 138 are surrounded by and sealed within a second internal powerbox housing 172 within housing 122. Further, the sealing locations of the powerbox housing 172 are generally "behind" the tube-engaging members 138. This arrangement helps prevent possible entry of fluid into the powerbox housing 172. However, in rare instances of fluid entry, weep holes 214 are located in the front housing 122 in locations connected to the interior of the powerbox housing 172 for cleanout purposes. See FIG. 2B. This arrangement enables a tubing assembly 136 to snap into place adjacent the tube-engaging members 138 and powerbox housing 172 such that the interior of the full housing 122 is insulated from any possible leaks or fluid damage. In the event of tubing failure, any fluid leakage would be contained by the powerbox housing 172. Having the seals of the powerbox housing "behind" the tube-engaging members 138 can be advantageous over prior designs where the seals are in the front exterior of pump housings.

In general, the housing and seal arrangements are structured for relative simplicity and require relatively few parts compared to other volumetric pumps. For example, sealing via a central mount 215 in the assembly receptacle 134 creates a "sandwich" or physical configuration at least partially around the front housing 122 to hold the powerbox 172. This arrangement provides an easily accessible location and can be convenient for maintenance and serviceability.

Although the camshaft assembly 154 primarily resides within powerbox housing 172, the ends of the camshaft 164 extend beyond each of the respective side walls 202 and 204. (Also See FIG. 3, for example) The portion of the camshaft 164 extending beyond side 202 includes a disc 216 of an electro-optical sensor that enables sensing of camshaft position. Other types of sensors to detect camshaft position are contemplated as well. In some embodiments, an encoder (not shown) can be associated with the motor 152 to further measure and refine the camshaft position within the cam cycle with an even higher degree of precision. This can provide closed loop control of the pump 102 in some embodiments. In some embodiments, the encoder can merely be used as a safety verification of the camshaft position, as determined by the optical sensor and disc 216, for example.

The portion of the camshaft 164 extending beyond side 204 includes a helical cam gear 158. This helical cam gear 158 is driven by a helical motor gear 156. Helical motor gear 156 is rotated by stepper motor 152. Operation of the stepper motor 152 is described later in greater detail. While gears 156 and 158 are not contained within the powerbox housing 172, these gears are protected by an intermediate support structure 217 (Also See FIG. 3, for example), functioning as a gearbox, that extends between the rear powerbox housing 160 and the motor 152. This intermediate support structure 217 may be integrally formed with the rear powerbox housing 160 in some embodiments. The intermediate support structure 217 does not fully encapsulate the gears 156 and 158, but does generally shield these components from interference or disruption.

Other interior features shown around the drive-train assembly 150 in FIG. 2E include a pair of speakers 130, an electrical assembly 218, an I/O interface port 132, and a plurality of fasteners 188 (generally screws or bolts). Various other features will be present in the front assembly portion 120, but are not specifically shown in FIG. 2E. These include any other suitable components necessary for control, operation, power and display of information for a peristaltic pump 102.

Details related to the drive-train assembly 150 and its operation are discussed below with respect to FIGS. 3-9. Each of these figures shows a partial view of certain components of the drive-train assembly 150 and has removed various obstructing features such that the individual components and features of the drive-train assembly 150 can be better understood.

Figure 3:
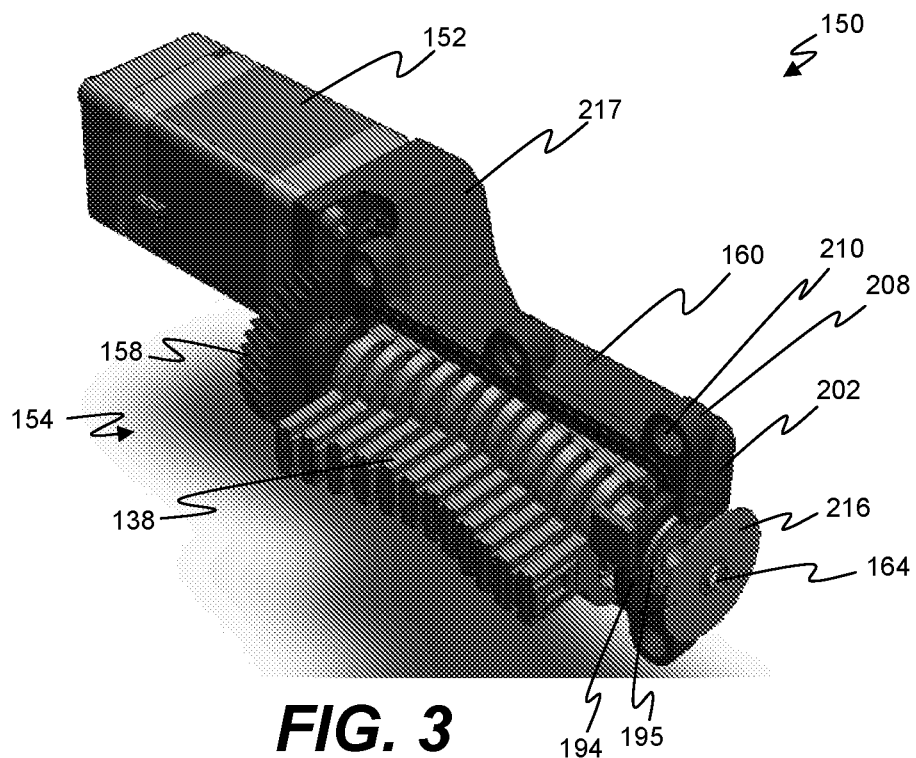
FIG. 3 is a perspective view of an isolated partial drive-train assembly of an LVP, according to an embodiment.

FIG. 3 is a perspective view of an isolated partial drive-train assembly 150 of a pump 102. In general, the drive-train assembly 150 is largely made up of a motor 152 and a camshaft assembly 154. Motor 152 is generally a stepper motor with a gear shaft. Motor 152 drives helical motor gear 156, which in turn drives helical cam gear 158, which in turn rotates the camshaft 164 and operates the camshaft assembly 154.

The stepper motor 152 is controlled such that a high level of flow constancy is achieved from its manipulation of the associated camshaft assembly 154. In general, this type of flow constancy provides constant and accurate infusate delivery. This constancy of flow is largely achieved by carefully controlled movement of the camshaft, including rapidly speeding up the motor during the brief periods during the cam cycle in which little or no infusate is being delivered based on movement of the tube-engaging members 138. The controls of the motor 152 are later discussed in greater detail. The power source and controls for the stepper motor are not specifically depicted here, but should be readily understood to be present in or provided via the internal portion of the pump 102 that is not specifically depicted in the front assembly portion 120 shown in FIGS. 2A-E.

Figure 6:
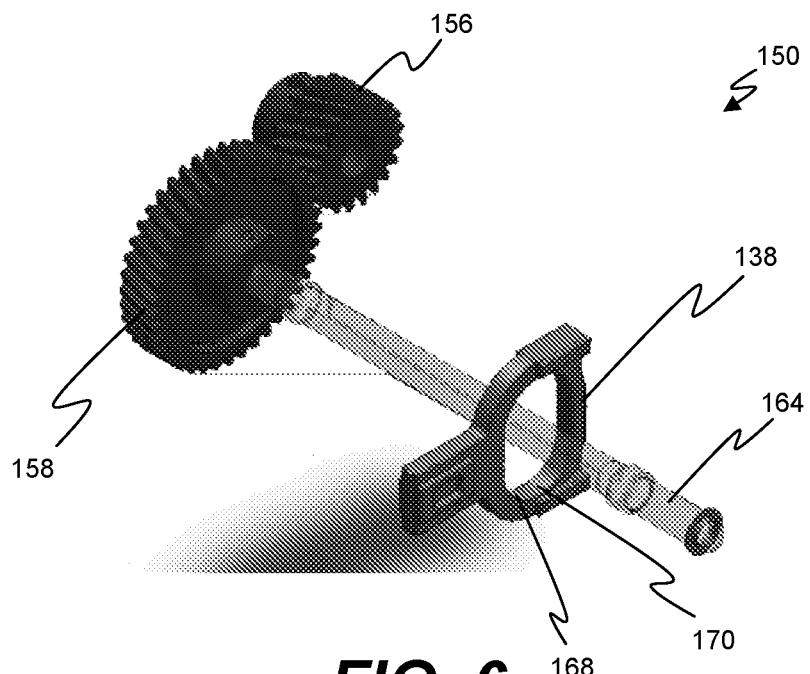
FIG. 6 is a perspective view of an isolated partial drive-train assembly of an LVP, according to an embodiment.

In FIG. 3, camshaft assembly 154 is shown situated in rear powerbox housing 160, but with front powerbox housing 162 and associated components removed. Accordingly, the general arrangement of the gears 156 and 158, camshaft 164, tube-engaging members 138, camshaft support bearings 195, seals 194, and disc 164 is shown. The tube-engaging members 138 are largely located within the rear powerbox housing 160 while the gears 156 and 158 are located in the intermediate support structure 217. Similarly, FIG. 4 provides a perspective view of a partial isolated drive-train assembly 150 in which the rear powerbox housing 160 is removed. FIG. 5 provides a perspective view of a partial isolated drive-train assembly 150 in which the tube-engaging members 138 are not shown as well. FIG. 6 provides a perspective view of a partial isolated drive-train assembly 150 in which only a central axial portion of the camshaft 164 is shown relative to a tube-engaging member 138.

From the various views in FIGS. 3-6, the drive-train assembly 150 and its arrangement of parts can be better understood. As shown, camshaft assembly 154 includes a unitary camshaft 164 that includes a varying profile of integral, similar, segmented cam portions 166 (see FIG. 5). In various embodiments, the segmented cam portions 166 provide a camshaft 164 with twelve identical lobes. The lobes are uniformly distributed as they are each clocked thirty degrees apart from the adjacent lobes on either side. Proximate both ends of the camshaft 164, and outside segmented cam portions 166, are rotating camshaft support bearings 195 (See FIG. 4, for example). These camshaft support bearings 195 permit axial, rotational movement of the camshaft 164. Camshaft support bearings 195 are mounted within the curved slots 192 and 212 (See FIG. 2E) of the powerbox housings 162 and 160. The camshaft support bearings 195 are sealed to the powerbox housings 160 and 162 by semi-circular seals 194.

Surrounding the segmented cam portions 166 of the camshaft 164, are twelve tube-engaging members 138 that cooperatively move according to rotation of the camshaft 164. More specifically, the tube-engaging members 138 each contain an internally defined aperture 168 through which the camshaft 164 passes. Interaction of the segmented cam portions 166 of the camshaft 164 with the respective interior perimeter surface 170 of the internally defined aperture 168 governs movement of the tube-engaging member 138.

Figure 7A:
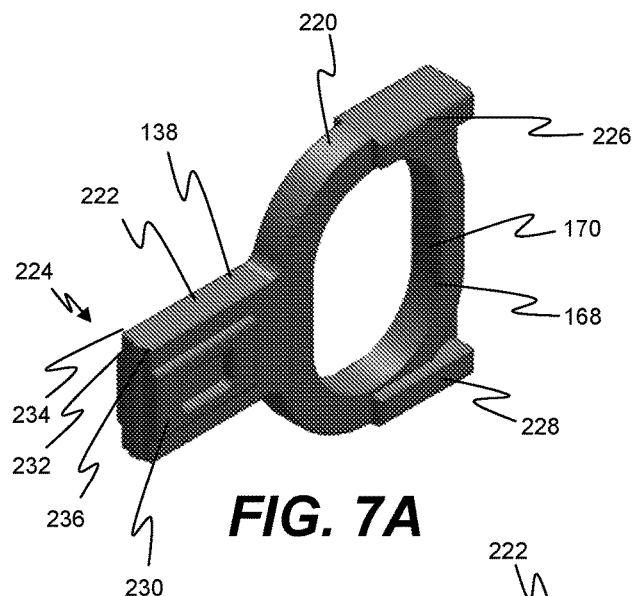
FIG. 7A is a perspective view of a tube-engaging member of an LVP, according to an embodiment.
Figure 7C:
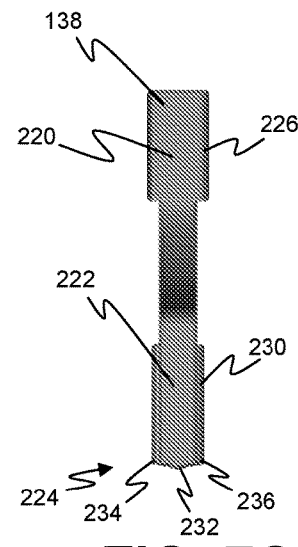
FIG. 7C is a top view of a tube-engaging member of an LVP, according to an embodiment.
Figure 7B:
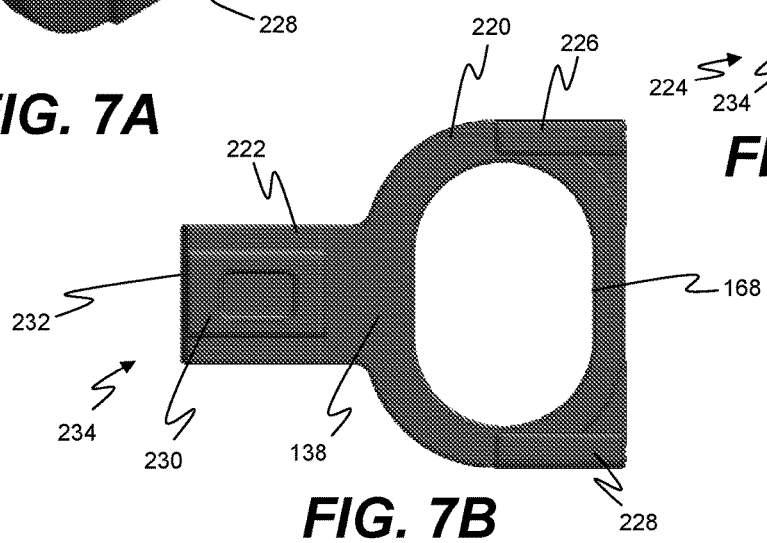
FIG. 7B is a side view of a tube-engaging member of an LVP, according to an embodiment.

FIGS. 7A-C and 8 show specific details regarding the structure and operation of the tube-engaging members 138 (sometimes referred to as "fingers"). FIG. 7A is a perspective view of a tube-engaging member 138 of a pump 102. FIG. 7B is a side view of a tube-engaging member 138, and FIG. 7C is a top view of a tube-engaging member 138. In the embodiments of the pump 102 described in this application, the camshaft assembly 154 contains twelve tube-engaging members 138. In other embodiments, fewer or additional tube-engaging members may be present together with an appropriate corresponding camshaft geometry. In general, the number of tube-engaging members 138 helps determine quantities of fluid delivery per rotation or the "packet size" of fluid being delivered. Packets may be thirteen microliters in some embodiments, for example. In some embodiments, each of the tube-engaging members 138 can be uniform and identical in shape, as shown in FIG. 7A.

In general, the tube-engaging members 138 have a plate-like, key-shaped profile including a rear head portion 220, and a rectangular front shaft portion 222 that culminates in an engagement end 224. The head portion 220 constitutes a larger bowed shape containing a central internal oval-shaped cam aperture 168. Interior perimeter surface 170 defines the inside edge of the cam aperture 168 and provides a surface for the segmented cam portions 166 of camshaft 164 to move against. To aid in spacing and prevent wear between adjacent tube-engaging members 138, blocks constituting top and bottom wear surfaces 226 and 228 protrude from the sides of the tube-engaging members 138 at upper and lower locations.

Figure 8:
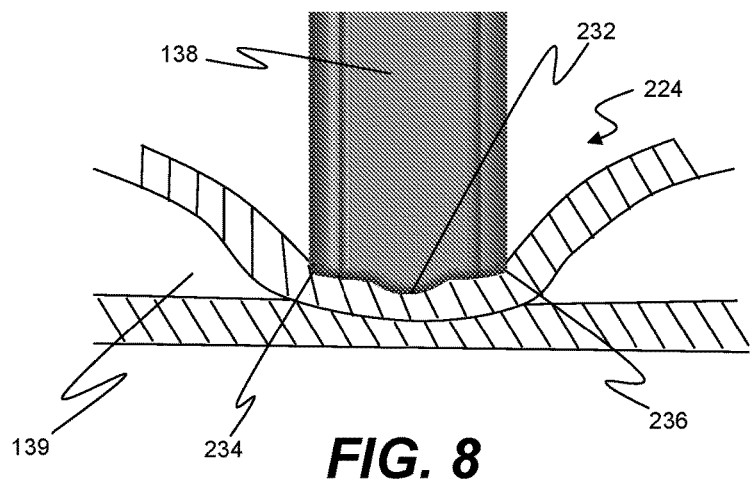
FIG. 8 is a top view of the end of a tube-engaging member of an LVP occluding a tube, according to an embodiment.

The rectangular front shaft portion 222 of the tube-engaging members 138 includes shaft wear plates 230 protruding from each side of the front shaft portion 222 to further aid in spacing and to prevent wear between adjacent tube-engaging members 138. The rectangular front shaft portion 222 also includes an engagement end 224 with a central rounded protrusion 232 and two rounded corner portions 234 and 236 on the ends of the shaft wear plates 230 that aid in tube occlusion. The central rounded protrusion 232 and rounded corner portions 234 and 236 cooperate to reduce wear on a tube 139 being occluded in the pump 102, as shown in FIG. 8, for example. Specifically, the rounded corner portions 234 and 236 prevent concentrating all the pressure exerted by the tube-engaging members 138 at the central rounded protrusion 232 or other single point of contact. Accordingly, the plurality of tube-engaging members 138 each have an engagement end 224 shaped for tube contact including a central rounded protrusion 232 as well as secondary rounded portions 234 and 236 on either side of the central rounded protrusion 232.

In general, the geometries of the tube-engaging members 138 serve to reduce noise in the camshaft assembly 154. Lubricious materials are generally used to construct tube-engaging members 138 to avoid noise and friction of moving parts. Additionally, as seen in FIG. 2B, ribs 238 define and surround the top and bottom of the opening 174 in the assembly receptacle 134 of the pump 102. In general, ribs 238 provide grooves that function as guides and reduce movement and rattling of the tube-engaging members 138. Specifically, outwardly protruding engagement ends 224 of tube-engaging members 138 sit in the ribbed grooves formed by the ribs 238. Ribs 238 serve as guides for movement of the tube-engaging members 138. Also shown in FIG. 2B (and also FIG. 11) are the horizontal protruding "rail guides" 240 and 242, present above and below the opening 174. Rail guides 240 and 242 serve to prevent tube walk (i.e. up and down tube movement) as well as to provide a consistent contact surface for the rigid, but spring-biased, pressure plate 244 to engage. Specifically, rail guides 240 and 242 include three contact features 243a, 243b, 243c which protrude outwardly from the rail guides (i.e. one contact features 243a near the middle of the upper rail guide 240 and one contact point 243b, 243c at each end of the lower rail guide 242). These three contact points form a plane providing a dependable, well-defined, location for pressure plate 244 relative to the tube-engaging members 138 and the other components of the assembly receptacle 134 when the receptacle door 112 of the pump 102 is closed. Accordingly, in various embodiments, a suspended rigid pressure plate 244 for tube compression is located on a receptacle door 112 that is hinged adjacent the assembly receptacle 134. In various embodiments, the assembly receptacle 134 includes a set of horizontally-disposed guide rails 240, 242 located above and below the tube-engaging members 138 to prevent vertical tube walk and including three projections or contact features 243a, 243b, 243c to define planar contact with a suspended pressure plate.

FIG. 8 is an example of a close-up top view of the engagement end 224 of tube-engaging member 138 of a pump 102 that is in the process of occluding a tube 139. Despite the general top view depicted, the tube 139 is shown in a cross-sectional view for clarity. As shown, the tube 139 is occluded by the central rounded protrusion 232 as well as the rounded corner portions 234 and 236 of the shaft wear plates 230. The rounded central protrusion 232 and rounded corner portions 234 and 236 cooperate to reduce wear on tube 139 as the rounded corner portions 234 and 236 absorb some of the pressure exerted by the tube-engaging members 138. With this arrangement, exerted pressure is not merely transferred as a single point load at the central rounded protrusion 232. As shown, the central rounded protrusion 232 is dimensioned to protrude further than the secondary rounded corner portions 234 and 236 but less than an amount necessary to fully occlude a tubing assembly without contact of the tube 139 being made by the secondary rounded features as well.

The distal geometry of a tube-engaging member 138 creates an area for displacement of tube 139 thereinto, from areas of energy concentration. Thus, abrasion and other deleterious forces are minimized and life of the administration set 104 is increased. As shown in FIG. 8, the distal end of the tube-engaging member 138 is in contiguous juxtaposition, at least substantially if not entirely, with the surface of the tube 139 upon which it is pressing.

Figure 9:
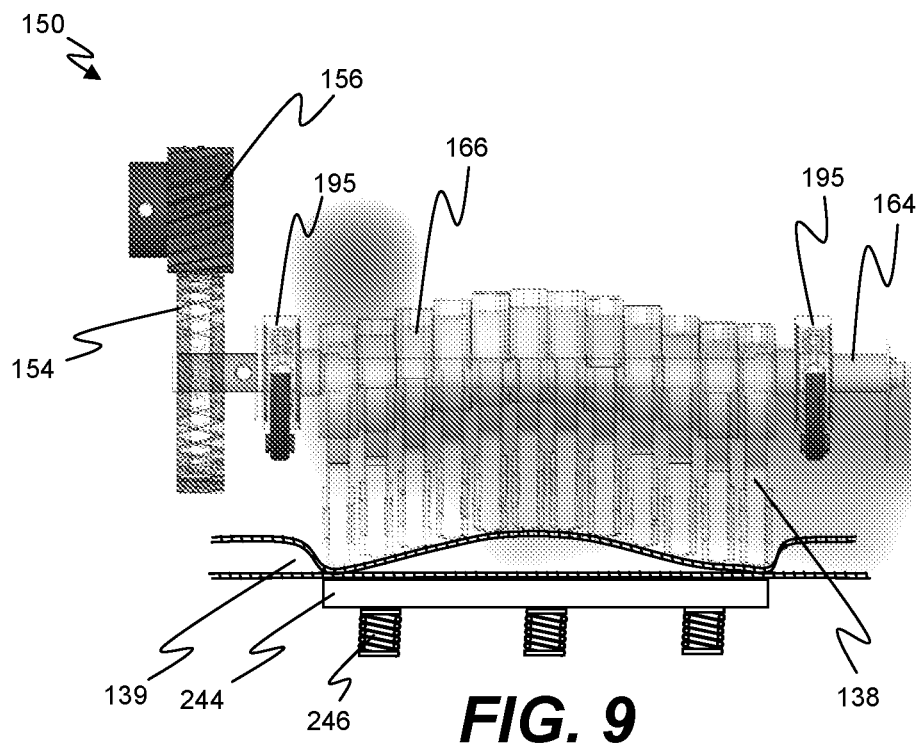
FIG. 9 is a top view of a full set of tube-engaging members of an LVP disposed on the camshaft of a drive-train assembly illustrating occlusion of a tube against a pressure plate, according to an embodiment.

FIG. 9 is a top view of a set of tube-engaging members 138 disposed on the camshaft 164 of a drive-train assembly 150 located adjacent a tube 139 and pressure plate 244 illustrating the general peristaltic pumping arrangement of a pump 102. Despite the general top view depicted, various components, including tube 139, pressure plate 244, and springs 246 are shown in cross-section for clarity. In general, when the camshaft 164 is driven to rotate, the segmented cam portions 166 rotate in the cam apertures 168 of the respective tube-engaging members 138. The tube-engaging members 138 successively advance fluid down the tube 139 from one tube-engaging member 138 to the next in a waved manner.

The engagement ends 224 of tube-engaging members 138 may be designed to over-travel beyond full tube occlusion in some embodiments. See FIG. 9. In some embodiments, the over-travel distance can be one additional wall thickness. Other amounts of longer or shorter over-travel are contemplated as well. This over-travel can be done for safety as it is important to ensure that occlusion completely takes place at the appropriate times and that free-flow is prevented. To the extent that there is excessive extension or travel of the tube-engaging members 138, this extension is absorbed by the suspended pressure plate 244. Specifically, the pressure plate 244 is coupled to the inside of receptacle door 112 and is biased forward by a plurality of springs 246 located within receptacle door 112.

Figure 10:
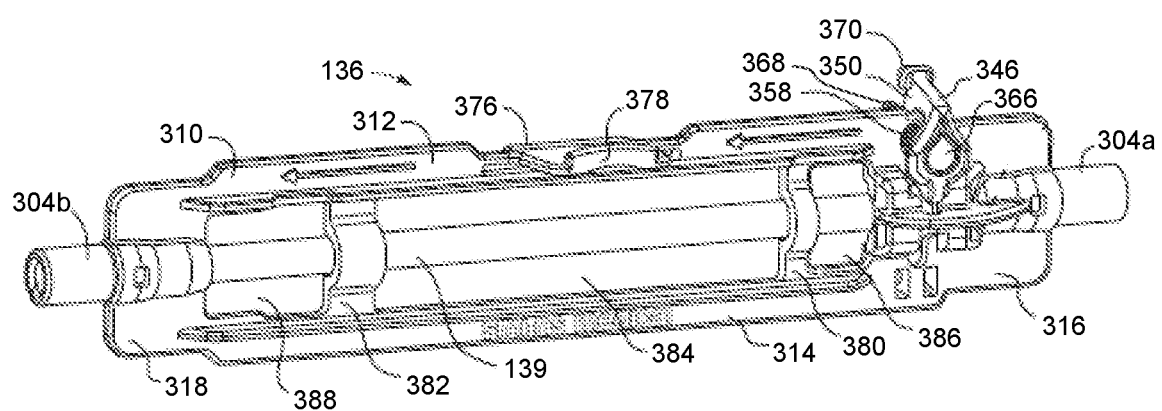
FIG. 10 is a front perspective view of an assembly of a portion of an administration set, according to an embodiment.

FIG. 10 generally illustrates a front perspective view of an assembly 136 of an administration set 104. Assembly 136 can include a peristaltic tube 139 formed of a resilient material that is suitable for compression (and recovery from compression) by the linear peristaltic pump drive of pump 102. In some embodiments, peristaltic tube 139 is formed from silicone. In other embodiments, polyvinyl chloride, polyurethane, latex rubber, or any other suitable compressible resilient material can be used. At opposing ends of peristaltic tube 139, assembly 136 can include first and second tube couplers 304a, 304b. Tube couplers 304a, 304b can function to fluidically couple the peristaltic tube 139 with upstream tubing 140 and downstream tubing 144 illustrated in FIG. 1.

As illustrated in FIG. 10, assembly 136 can include a frame 310 configured to receive tube couplers 304a, 304b and thereby substantially hold peristaltic tube 139 when coupled to the tube couplers, in a substantially defined position relative to frame 310. Frame 310 can include a first beam 312 and can also include a second beam 314 that is substantially parallel to first beam 312.

At a first end, frame 310 can include a first end plate 316 joining first and second beams 312, 314, with first end plate 316 substantially lying in the first plane of first and second beams 312, 314. At a second end, frame 310 can include a second end plate 318 joining first and second beams 312, 314, with second end plate 318 substantially lying in the first plane of first and second beams 312, 314. First end plate 316 and second end plate 318 can each define a channel configured to receive corresponding tube coupler 304a, 304b.

Components of assembly 136 can be structured and dimensioned such that, when assembly 136 is assembled, manufactured, or otherwise produced, peristaltic tube 139 is maintained in position with respect to frame 310 such that it is held essentially straight between tube couplers 304a and 304b. This can help ensure that tube 139 is properly positioned and aligned with respect to pump 102 and components of pump 102 that interact with tube 139 when assembly 136 is mated thereto or installed therein. The length of peristaltic tube 139 can be specified with tolerances to achieve this essentially straight positioning. The length of tube 139 at maximum tolerance can be such that there will be essentially no slack or buckling in the tube when assembled into assembly 136. At shorter lengths than maximum tolerance, such as a minimum tolerance, peristaltic tube 139 can be assembled into assembly 136 with a small amount of tension, slightly stretched between tube couplers 304a and 304b (between the first and second tube supports).

With reference to FIG. 10, assembly 136 can include features to selectively prevent free-flow of infusate through the peristaltic tube 139. Assembly 136 can include a free-flow prevention (FFP) arm 346 that can be coupled to frame 310 and that can include a latching structure 350. Arm 346 can be hingedly coupled to frame 310.

FFP arm 346 can be selectively movable relative to frame 310 between a free-flow preventing position and a free-flow allowing position. Assembly 136 can include a biasing mechanism configured to bias FFP arm 346 to the free-flow preventing position. Assembly 136 can include, for example, a spring 358 that can exert forces on frame 310 and FFP arm 346 to bias arm 346 to the free-flow preventing position. Spring 358 can be captured between frame 310 and FFP arm 346.

With regard to the potentially ergonomic manipulability of the latching mechanism, latching structure 350 of FFP arm 346 can include a thumb press surface 366 and the latching receiver can include a finger press surface 368. The finger press surface 368 of the latching receiver and the thumb press surface 366 of the latching structure 350 are oriented in an oppositely-disposed manner. The opposing interaction of the latching structure 350 and the latching receiver separated by spring 358 provides an arrangement in which the finger press surface 368 and the thumb press surface 366 are operatively coupled with one another in close proximity. By manipulating thumb press surface 366 and finger press surface 368 and manually squeezing or urging surface 368 toward surface 366, the latching mechanism can be urged relatively easily and ergonomically into the latched state.

The latching mechanism also can be relatively easily and ergonomically manipulated to release the mechanism from the latched state or to unlatch FFP arm 346 such that it can be moved (by, for example, a biasing force of spring 358) to the free-flow preventing position. To aid such a release manipulation, latching structure 350 of FFP arm 346 can include a release catch 370 that a fingertip can exert force against to release latching structure 350 from latching surface 362. Release catch 370 can be structured to provide purchase or a suitable surface thereon for a human finger to flex FFP arm 346 sufficiently to unlatch the latching mechanism. Release catch 370 can include one or more side extensions that extend to one or both sides of FFP arm 346, somewhat resembling a cross-bar of the letter "T" in the illustrated embodiment.

Figure 11:
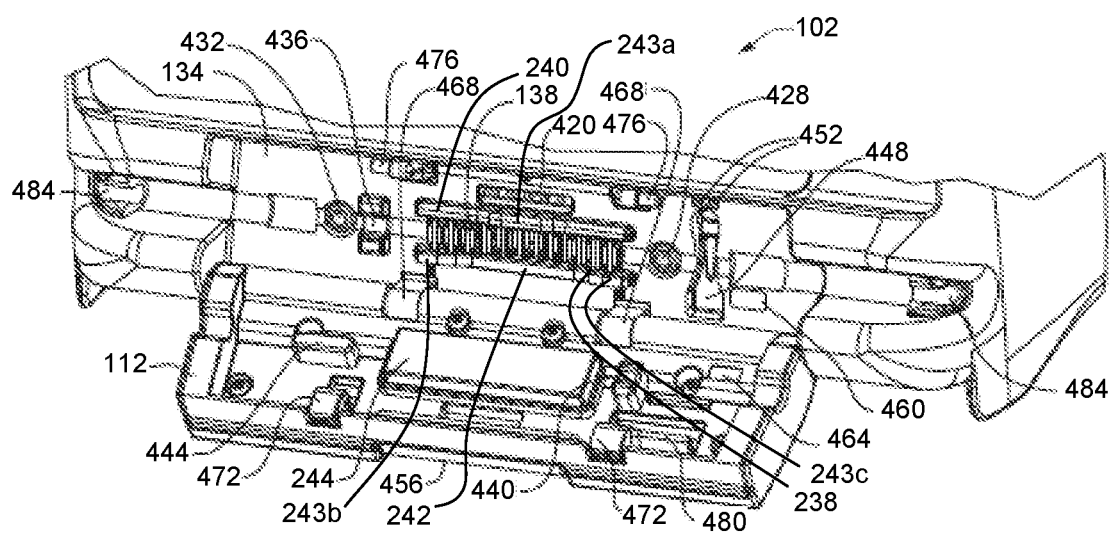
FIG. 11 is a schematic perspective view of portions of an example LVP, particularly illustrating details of an assembly receptacle and a receptacle door, according to an embodiment.
Figure 12:
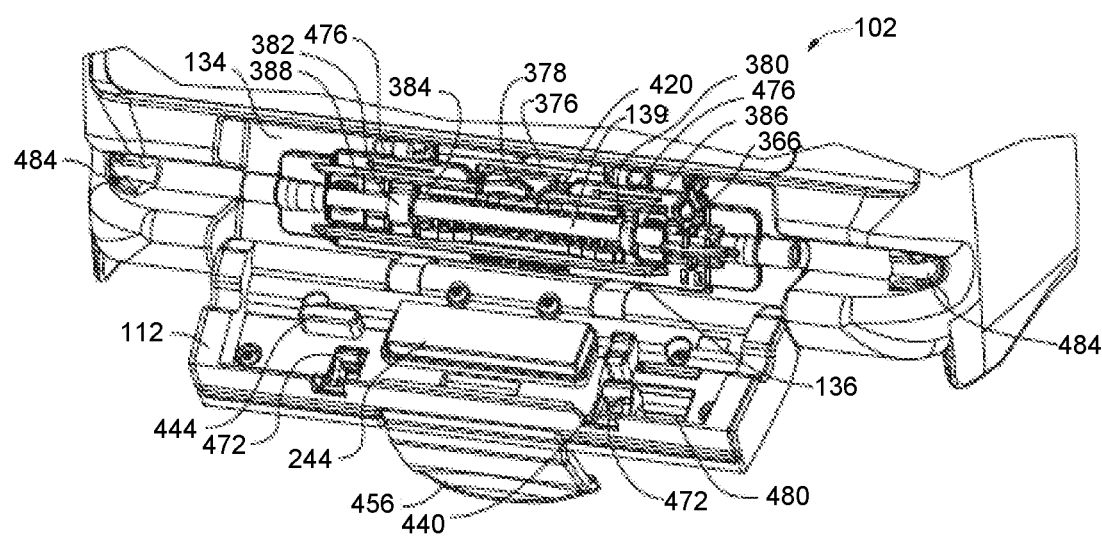
FIG. 12 is a schematic perspective view of portions of an example LVP, with a portion of an administration set received by the assembly receptacle, according to an embodiment.

FIG. 11 is a schematic perspective view of portions of a peristaltic infusion pump 102, of peristaltic infusion pump system 100, particularly illustrating details of an assembly receptacle 134 and a receptacle door 112 of the pump 102. Assembly receptacle 134 can be configured to receive assembly 136 of administration set 104 such that the set 104 is thereby operatively coupled to pump 102. FIG. 12 is a schematic perspective view of portions of peristaltic infusion pump 102 of FIG. 11, with assembly 136 received by or installed in assembly receptacle 134. In FIGS. 11 and 12, receptacle door 112 of pump 102 is in an open position.

Frame 310 of assembly 134 can include a snap-fit tab 376 (see FIG. 10) configured to securely and releasably attach to snap-fit opening 420 of assembly receptacle 134 (as shown in FIG. 11), such that assembly 136 is thereby releasably secured to assembly receptacle 134, and accordingly, administration set 104 can thereby be operatively coupled to pump 102. Snap-fit tab 376 can be formed integrally or otherwise provided with first beam 312 of frame 310, and project away from the first plane of first beam 312 and second beam 314 in a first direction that can be substantially or approximately perpendicular to the first plane. A snap release handle 378 (see FIG. 10) can be formed integrally or otherwise provided with first beam 312, with release handle 378 operatively coupled to tab 376. Release handle 378 can project away from the first plane in a second direction generally opposing the first direction, but other configurations are possible. First beam 312 can incorporate features to provide flexibility for tab 376 and handle 378 relative to other portions of beam 312, such as narrowing of the beam and/or structuring the beam as multiple sub-beams, as illustrated.

Snap release handle 378 and snap-fit tab 376 can be structured such that a defined manipulation of handle 378 can move tab 376 relative to snap-fit opening 420 of assembly receptacle 134 such that tab 376 is releasable from opening 420, and hence assembly 136 is thereby releasable from assembly receptacle 134. The defined manipulation can be, for example, to press or otherwise move snap release handle 378 in a downward direction relative to snap-fit opening 420 of assembly receptacle 134, which can result in snap-fit tab 376 moving upwardly relative to opening 420 of receptacle 134, as handle 378 and tab 376 together flexibly rotate relative to first beam 312. Movement of snap-fit tab 376 upwardly relative to snap-fit opening 420 of assembly receptacle 134 can be such that tab 376 is thereby released from opening 420. In addition, snap-fit tab 376 can be configured such that release from snap-fit opening 420 does not necessarily require that the snap release handle 378 be manipulated. For example, in some instances release of assembly 136 from assembly receptacle 134 can be achieved by pulling tubing (such as upstream tubing 140 and/or downstream tubing 144) away from pump 102. The structural configuration of snap-fit tab 376 may allow it to release from snap-fit opening 420 under the forces existing in such a scenario.

When assembly 136 is secured to assembly receptacle 134 via snap-fit tab 376 of assembly 136 and snap-fit opening 420 of receptacle 134 in pump 102, peristaltic tube 139 of assembly 136 can be positioned for engagement with tube-engaging members 138 of a linear peristaltic pump drive of pump 102. Tube-engaging members 138, twelve members in the illustrated example of FIGS. 11 and 12, can be driven in a coordinated manner by elements of a linear peristaltic pump drive of pump 102 to thereby urge, push, or transport infusate through, squeezingly, peristaltic tube 139 and thus responsively through other tubes or lines connected fluidically thereto such as upstream tubing 140 and downstream tubing 144 of infusion system 100 illustrated in FIG. 1.

As illustrated in, e.g., FIG. 10, frame 310 of assembly 136 can include further structures to assist in maintaining a desired position of peristaltic tube 139, such as an upstream cross-support 380 and a downstream cross-support 382 that can span from first beam 312 to second beam 314. Each cross-support 380, 382 can include a curved section to cradle or otherwise supportingly hold peristatic tube 139. When assembly 136 is secured to assembly receptacle 134 in pump 102, cross-supports 380, 382 can also assist in maintaining a proper positon of peristatic tube 139 relative to tube-engaging members 138 of pump 102 such that members 138 are able to effectively engage tube 139.

First beam 312, second beam 314, upstream cross-support 380, and downstream cross-support 382 can define, surround, or bound a pump tube opening or "window" 384 of frame 310. Pump tube window 384 can be substantially free of any structure of assembly 136 other than a portion of peristaltic tube 139 therewithin and generally can correspond to an area where tube-engaging members 138 of pump 102 can engage tube 139 when assembly 136 is secured to assembly receptacle 134 of pump 102. As illustrated in FIG. 11, receptacle door 112 of pump 102 can include a pressure plate 244 that can be, when door 112 is closed and secured, positioned along tube 139 generally opposite tube-engaging members 138 such that tube 139 is located between pressure plate 244 and tube-engaging members 138. When in such a configuration, pump 102 and assembly 136 can be structured such that, in an example embodiment, tube-engaging members 138 and pressure plate 244 substantially do not contact frame 310.

As illustrated in, e.g., FIG. 10, portions of frame 310 can define, surround, or bound further windows or openings that can correspond to other areas where components of pump 102 can engage with peristaltic tube 139. For example, first beam 312, second beam 314, upstream cross-support 380, and first end plate 316 can define, surround, or bound an upstream sensor opening or "window" 386 of frame 310. First beam 312, second beam 314, downstream cross-support 382, and second end plate 318 can define, surround, or bound a downstream sensor opening or "window" 388 of frame 310. Pump 102 can include any or all of, in receptacle 134, an upstream occlusion sensor 428, a downstream occlusion sensor 432, and an air-in-line detector 436, although this is not limiting and other locations, combinations, or arrangements of sensors can be included with pump 102. Upstream sensor window 386 can be substantially free of any structure of assembly 136 other than a portion of peristaltic tube 139 and generally can correspond to an area where upstream occlusion sensor 428 can engage tube 139 when assembly 136 is secured to assembly receptacle 134 of pump 102. Downstream sensor window 388 can be substantially free of any structure of assembly 136 other than a portion of peristaltic tube 139 and generally can correspond to an area where downstream occlusion sensor 432 and/or air-in-line detector 436 can engage tube 139 when assembly 136 is secured to assembly receptacle 134 of pump 102.

Receptacle door 112 of pump 102 can include tube supports 440, 444 that can be, when door 112 is closed and secured about assembly 136, positioned along tube 139 generally opposite, respectively, upstream occlusion sensor 428, and downstream occlusion sensor 432 and air-in-line detector 436, such that tube 139 is located between tube supports 440, 444 and occlusion sensors 428, 432, and air-in-line detector 436. When in such a configuration, pump 102 and assembly 136 can be structured such that, in an example embodiment, sensors 428, 432, detector 436, and tube supports 440, 444, substantially do not contact frame 310. In other embodiments, an assembly similar to assembly 136 can include tubing supports that can provide preload between a peristaltic tube and pump sensors/detectors. Such tubing supports could be included with a frame similar to frame 310 of assembly 136.

As illustrated in, e.g., FIG. 11, assembly receptacle 134 of pump 102 can include features to accommodate and interact with FFP arm 346 of assembly 136. In particular, surfaces of assembly receptacle 134 can define, surround, or bound a recess 448 dimensioned to permit generally unhindered motion of the FFP arm 346 between free-flow preventing and a free-flow allowing positions when assembly 136 is installed in pump 102. Toward a top portion of recess 448, surfaces of assembly receptacle 134 can include at least one latch ramp 452. Latch ramp(s) 452 in receptacle 134 of pump 102 and release catch 370 of assembly 136 can be structured to cooperate so that when assembly 136 is placed in and/or secured to assembly receptacle 134, a portion or portions of release catch 370 (such as side extensions thereof) substantially slide along latch ramp(s) 452 as FFP arm 346 of assembly 136 is moved toward the free-flow allowing position. Contact forces thus exerted on release catch 370 of FFP arm 346 by latch ramp(s) 452 during such sliding interactions can flex the arm 346 sufficiently to prevent the latching mechanism from latching in the free-flow allowing position. As discussed elsewhere herein, FFP arm 346 can be moved toward the free-flow allowing position when receptacle door 112 is closed and a door latch lever 456 is moved from its unlatched position to its latched position. Latch ramp(s) 452 can substantially inhibit or prevent the latching mechanism from latching in the free-flow allowing position during such an action. Furthermore, if the latching mechanism is latched in the free-flow allowing position before assembly 136 is secured to assembly receptacle 134, then when assembly 136 is secured to receptacle 134 (by pressing snap-fit tab 376 into snap-fit opening 420 as aforedescribed), latch ramp(s) 452 can exert force on release catch 370 sufficient to flex FFP arm 346 enough that the latching mechanism is released, thereby allowing FFP arm 346 to be biased (for example, by spring 358) to the free-flow preventing position. This can be an important safety feature, helping to ensure that administration set 104 is in a non-free-flow state initially when it is secured to the pump.

As illustrated in, e.g., FIG. 11, assembly receptacle 134 of pump 102 can include an optical device 460 that can be configured and used to detect a presence of and/or identify a particular or different type or unit of assembly 136 received by assembly receptacle 134 of pump 102. An optical reference/calibration portion 464 can be included in or on door 112, generally within view of optical device 460 when door 112 is closed and assembly 136 is not received by assembly receptacle 134.

Door 112 is designed to be a field replaceable unit ("FRU"), meaning that it can be readily replaced should the door 112 be damaged. Further, because the door 112 is designed to be removable and replaceable the entire housing 122 need not be replaced, in the event of a compromised door. The door 112 is frangible in that it is designed to break or fail without impacting the remainder of the housing 122 as well.

After assembly 136 is received by assembly receptacle 134, door 112 can be rotated closed about hinges 468 (as shown in, e.g., FIG. 11) and door latch lever 456 can be moved from an unlatched position to a latched position. In FIGS. 11 and 12, door 112 can include one or more door latch hooks 472 corresponding to one or more door latch pins 476 of receptacle 134. Door latch hooks 472 can be mechanically linked to door latch lever 456 to responsively move as lever 456 is moved between latched and unlatched positions. When door 112 is closed and door latch lever 456 is in the latched position, door latch hooks 472 can be responsively positioned relative to door latch pins 476 to engagingly constrain or latch door 112 in the closed position. When door latch lever 456 is in the unlatched position, door latch hooks 472 can be responsively positioned to disengagingly not interfere with door latch pins 476 as door 112 is moved into and out of the closed position.

As also shown in FIGS. 11 and 12, door 112 can include an FFP arm pusher 480 that can be mechanically linked to door latch lever 456 to move as lever 456 is moved between latched and unlatched positions. In some embodiments, FFP arm pusher 480 can be provided integrally on a structure of door latch hook 472. FFP arm pusher 480 can be operatively coupled to door latch lever 456 and configured such that when assembly 136 is received by assembly receptacle 134 and door 112 is closed, FFP arm pusher 480 pushes FFP arm 346 (for example, by exerting force on arm 346 at thumb press surface 366 and/or other parts of arm 346) from the free-flow preventing position to the free-flow allowing position as door latch lever 456 is moved to the latched position. When door latch lever 456 is returned to the unlatched position, FFP arm pusher 480 can responsively retract, thereby allowing the biasing force provided by, for example, spring 358 to return FFP arm 346 to the free-flow preventing position.

At any suitable time, which may be before or after door 112 is closed, upstream and downstream tubing 140, 144 (not illustrated in FIG. 12) can be manually pressed into tube guides 484. Tube guides 484 capture the tubing that extends beyond either side of the frame 310 and tubing couplers 304a and 304b. Tubing guides 484 serve important tubing management functions that direct tubing away from the screen of the pump 102 or any other pumps 102 or equipment surrounding a patient. This convenient arrangement is especially useful for management of tubing in a vertically stacked group of pumps 102. A side view of tubing guide 484 show a "C" shaped tubing capture structure. Tubing guides 484 are located at the periphery of the housing 122 for retaining tubing 140 or 144 of a coupled administration set 104 beyond either side of the assembly receptacle 134. Only a small amount of force is needed to insert the tubing into tubing guides 484. This easy-to-mount aspect of assembly 136 lends itself to one-handed operation similar to the easy loading and removal design of the assembly 136 with respect to the pump 102. In some embodiments, engagement can be designed such that only fifteen Newtons of force or less is needed to load either the assembly 136 in the assembly receptacle 134 or load either of the and tubing 140 or 144 in its respective tube guide 484.

Figure 13:
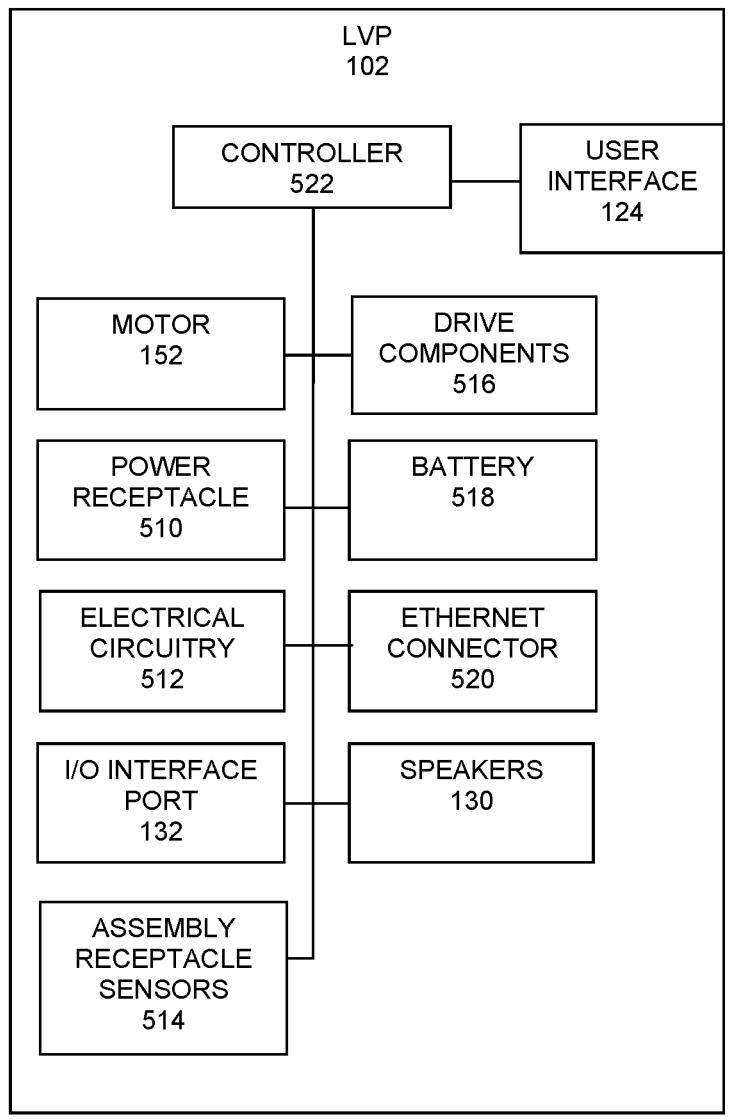
FIG. 13 is a general system diagram of an LVP, according to an embodiment.

FIG. 13 is a general system diagram of an LVP pump 102, including some components that are partially or fully obscured by the housing 122 or not depicted in the partial views in FIGS. 2A-E of the front assembly portion 120. The system diagram shows an LVP 102, including: user interface 124; speakers 130; I/O interface port 132; motor 152; power receptacle 510; electrical circuitry 512; assembly receptacle sensors 514; drive components 516; battery 518; Ethernet connector 520; and controller 522.

As discussed above, the user interface 124 serves as a source of data input for the LVP pump 102 from, for example, a medical clinician or pump programmer.

Although not specifically illustrated, user interface 124 can include a variety of touchscreen display, keypad or combination of these or other user interface technologies.

LVP pump 102 in FIG. 13 can include either line power, via a cord connected to a power receptacle 510 or via a connection member to a rack of infusion pumps that connects to the power receptacle 510. Battery 518 is another example of power to the LVP pump 102. A battery 518 can be fully enclosed in the housing 122 beneath a rear battery door cover, for example.

In FIG. 13, various electrical components and electrical circuitry 512 are located within the housing 122 for relaying or carrying out commands to the controller 522 or within the system. Various outside devices may be connected to the LVP 102 as well through inputs, such as Ethernet connector 520 or I/O interface port 132. The speakers 130 are equipped to provide a full range of audio output including commands, alerts, and informative communications. Assembly receptacle sensors 514 and other sensors can be part of the system as well. Assembly receptacle sensors 514, for example, can make various measurements for tasks such as sensing information about the particular tubing assembly 136. This can include sensing the route of infusion for which a particular tubing frame assembly is used. Sensors 514 can be optical sensors, RFID readers, etc. Controller 522 can utilize information gained from these sensors 514 and other components to assist in communications and decision-making in set-up and operations of pump 102.

Motor 152, as discussed earlier in this disclosure, is connected to the controller 522 and LVP pump 102 components generally. Motor 152 can be a stepper motor in some embodiments. Motor 152 can be the primary means for directing drive components 516 including the drive-train assembly 150 and, consequently, its tube-engaging members 138 within the assembly receptacle 134 against tube 139.

Controller 522 is connected to the user interface 124 and is responsible for ensuring that the LVP pump 102 is controlled in the desired manner. Controller 522 can be any suitable controller, microcontroller, microprocessor, or the like. Such a controller can include and/or be operatively coupled to any other hardware or software resource needed for its function, such as any suitable memory of any suitable capacity, containing any suitable software, firmware, operating parameters, and so on. The controller 522 can be configured and programmed to execute, command, and/or perform any suitable actions, tasks, steps, and/or methods for controlling the pump 102. The pump 102 can include a plurality of physically and/or logically distinct controllers, such as application-specific processors. In the present disclosure, a plurality of such controllers of a pump may be referred to collectively in the singular as the controller 522 of the pump 102. Methods of the present disclosure can be implemented by the controller 522 of the pump 102, and/or in some instances by another controller, such as by a controller of another pump, a system of pumps, a controller implemented on a server, or any other appropriate controller. As such, any reference in the present disclosure to a controller 522 in the singular should not be interpreted as strictly limiting to a single physical or logical controller (unless explicitly limited to a single controller), but rather, can include systems and/or methods in which controller 522 functions are provided by one or more controllers.

In various embodiments, the controller 522 can control the motor 152 and drive-train assembly 150 to achieve a relatively consistent flow of fluid infusate or "flow constancy". Typically, when delivering infusate to a patient, it is desirable to have the infusate be delivered at a relatively constant, unchanging rate. However, rotating the camshaft of a linear peristaltic mechanism at a constant rate may not result in delivery of infusate at a reliably constant rate. Therefore, it is desirable to continuously change the rotational speed of the camshaft 164 to compensate for the flow profile of the linear peristaltic mechanism. In general, to maintain a desired constant infusate delivery rate, rotational speed in positions where the flow profile is low or zero are increased. In areas where the flow profile is high, rotational speed is decreased.

Each revolution of the camshaft 164 can be resolved into a discrete number of positions (i.e. steps of the stepper motor 152). Rotational movement of the camshaft 164 to each of these discrete positions produces a distinct and different amount of volume to be delivered. At some positions, rotational movement of the camshaft 164 does not cause any fluid to be delivered at all.

By using knowledge of the flow profile, an optimal speed for each discrete position of the camshaft 164 can be determined for desired delivery rates (for example, a range of delivery rates between 0.1 mL/hr.-1200 mL/hr.). Once determined for a specific delivery rate, these varying camshaft rotational speeds can be repeated continuously within each revolution of the camshaft 164, thereby delivering infusate at a constant rate or nearly so.

Figure 14:
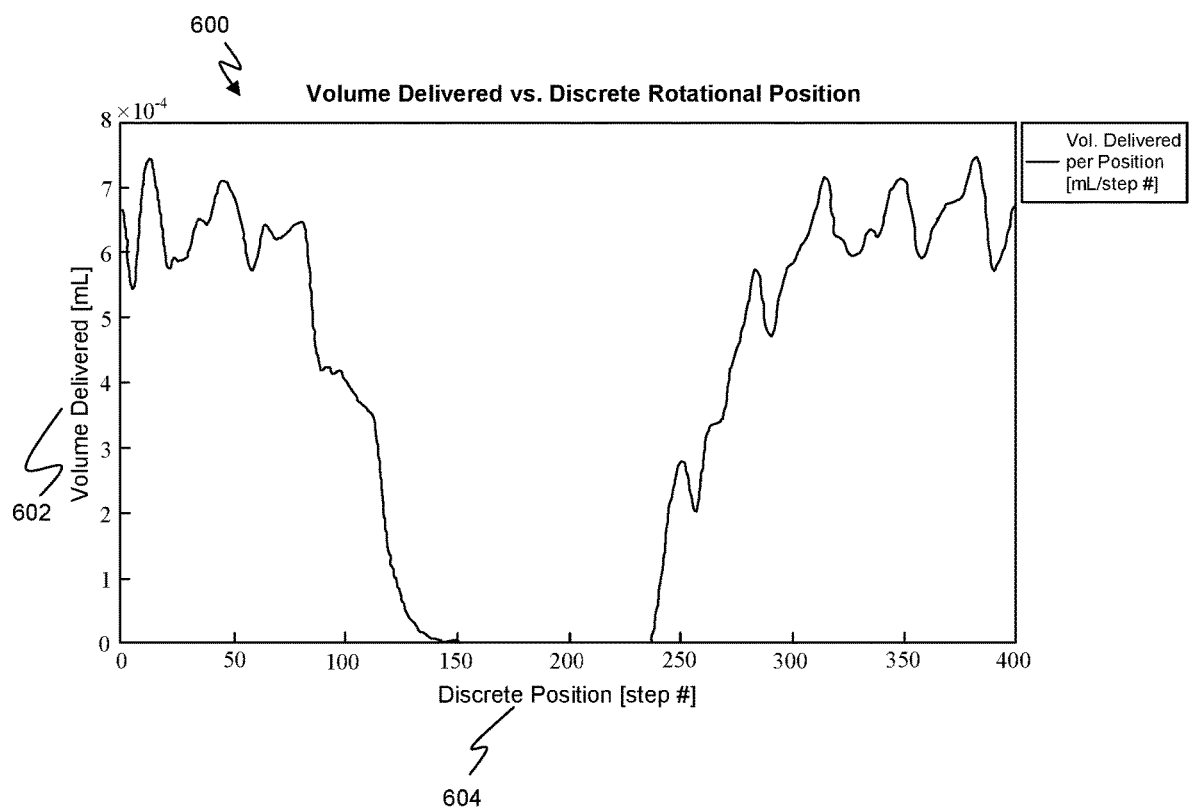
FIG. 14 is a chart showing a flow profile for an LVP of volume delivered per discrete rotational position of the camshaft, according to an embodiment.

FIG. 14 specifically illustrates an example of a flow profile 600 that can be utilized for various pumps 102. Volume delivered 602 is charted against discrete rotational position 604 (i.e., "step no."). In order to obtain the flow profile 600, a multitude of pumps 102 can be characterized. These pumps 102 take one full step (discrete position) every three seconds (an extremely slow rate) and their output (fluid delivery) is monitored at each position. For example, in an embodiment, each pump 102 completes a minimum of twenty full rotations (360 degrees each) of camshaft 164 (this can be a many hour test). The resulting fluid delivery at each of the discrete positions is determined by an average (for example, at least twenty data points go into each average from the minimum number of full camshaft rotations). By averaging across the multitude of pumps 102 that are characterized, an "average of averages" is obtained for the resulting volume delivered at each discrete position.

There are a few corrective measures that are taken into account in various embodiments as well. For example, a mathematical filter (moving average filter) can be applied during the process described above to address some noise concerns from the measurement system's output data. Further, a "percentage of difference" correction for each position's output volume can be applied to correct for the area of backflow where the flow profile of delivered volume is actually negative.

Once the resulting volume is known at each discrete position (sometimes called the step volume table), this information can be fed into (permanently stored in) the software for the pump 102. The pump software can use knowledge of a user's input delivery rate, the current position of the pump 102 within the mechanism cycle, and the step volume table to determine the speed at which to turn the motor 152 and therefore rotate the camshaft 164. The pump software also accounts for physical limitations of the motor 152 and drive system, like the maximum speed, maximum acceleration, and maximum deceleration. In this way, the software attempts to match the flow profile as close as possible subject to constraints. Both the total area under the curve (derivative) and the discrete position value are attempted to be matched as close as possible (again, subject to constraints). Accordingly, by this arrangement, the drive train assembly 150 is able to deliver infusate at a constant and reliable rate, or nearly so, from pump 102.

Various assemblies and methods for infusion system administration sets and infusion pumps are disclosed in PCT App. No. PCT/US2017/037929 to Adams et al., titled "Assemblies and Methods for Infusion Pump System Administration Sets", published as WO2017/218927 A1, which is hereby incorporated by reference. Various assemblies and methods related to housing arrangements for infusion pumps are disclosed in U.S. App. Ser. No. 62/534,407 and PCT App. No. PCT/US2018/042907 to Lacy et al., titled "Housing Arrangements for Infusion Pumps", which is hereby incorporated by reference.

Various embodiments of systems, devices, and methods have been described herein. These embodiments are given only by way of example and are not intended to limit the scope of the claimed subject matter. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed subject matter.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

What is claimed is:

1. A large volume pump (LVP) that provides peristaltic pumping to supply medical infusate, comprising:
a pump housing including an assembly receptacle,
a drive-train assembly configured for providing mechanical peristaltic movement, including:
a stepper motor, located within the pump housing; and
a camshaft assembly, driven by the stepper motor, including:
a unitary camshaft; and
a plurality of tube engaging members that cooperatively move according to rotation of the unitary camshaft, wherein a portion of each tube engaging member extends at least partially into the assembly receptacle;
a controller located within the pump housing that controls operation of the stepper motor and the camshaft assembly to move the plurality of tube engaging members in a peristaltic manner; and
a receptacle door coupled to the pump housing and including a door lever linked to a pusher, the receptacle door movable between an open position to allow access to the assembly receptacle and a closed position to block access to the assembly receptacle,
wherein, when an administration set tubing assembly is removably coupled in the assembly receptacle and the receptacle door in the closed position, the door lever is configured to be movable to a latched position such that the pusher mechanically contacts a free-flow protection arm of the administration set tubing assembly to move the free-flow protection arm to a flow-allowing position.

2. The LVP of claim 1, wherein the administration set tubing assembly that the assembly receptacle is configured to receive, includes:
a peristaltic tube suitable for compression by the drive-train assembly;
a first tube coupler and a second tube coupler, each attached at opposing ends of the peristaltic tube and each having a lumen in fluidic communication with the peristaltic tube;
a frame coupled to the first tube coupler and the second tube coupler at spaced-apart locations, the frame configured for releasable attachment to the LVP in which the peristaltic tube is positioned for engagement with the plurality of tube engaging members, the frame further including a latching receiver projecting from the frame having a finger press surface; and
wherein the free-flow protection arm hingedly is coupled to the frame and includes a latching structure sized to cooperate with the latching receiver.

3. The LVP of claim 1, wherein the pump housing includes a touch screen that permits operator interaction with the LVP.

4. The LVP of claim 1, wherein a suspended rigid pressure plate for tube compression is located on the receptacle door that is hinged to the pump housing adjacent the assembly receptacle.

5. The LVP of claim 4, wherein the assembly receptacle includes a set of horizontally-disposed guide rails located above and below the tube-engaging members to prevent vertical tube walk.

6. The LVP of claim 5, wherein the set of horizontally-disposed guide rails includes three projection features to define planar contact with the suspended rigid pressure plate.

7. The LVP of claim 1, wherein a second internal housing is included within the pump housing that largely surrounds the plurality of tube-engaging members, with only ends of the plurality of tube-engaging members extending out from the second internal housing through an opening into the assembly receptacle.

8. The LVP of claim 7, wherein the second internal housing is sealed at locations rearward of the tube engaging members to restrict possible fluid leakage from reaching further into the pump housing.

9. The LVP of claim 8, wherein weep hole apertures, that are connected to interior locations of the second internal housing, are located in the assembly receptacle at a front of the LVP pump.

10. The LVP of claim 1, wherein the controller controls the stepper motor to manipulate the camshaft assembly such that a relatively constant flow of medical infusate is provided by continuously changing rotational speeds of the camshaft assembly to compensate for the inconsistent flow profile of the drive-train assembly.

11. The LVP of claim 10, wherein the controller repeats the rotational speeds for the camshaft assembly within each revolution of the unitary camshaft.

12. The LVP of claim 1, wherein the camshaft has uniformly distributed lobes around a circumference of the camshaft.

13. The LVP of claim 1, wherein the plurality of tube-engaging members are of identical shape.

14. The LVP of claim 13, wherein the plurality of tube-engaging members each include shaft wear plates that protrude from each side of a front shaft portion to aid in spacing and prevent wear between adjacent tube engaging members.

15. The LVP of claim 14, wherein the plurality of tube-engaging members each include blocks providing top and bottom wear surfaces that protrude from each side at upper and lower locations to aid in spacing and prevent wear between adjacent tube engaging members.

16. The LVP of claim 15, wherein the plurality of tube-engaging members include twelve tube-engaging members.

17. The LVP of claim 1, wherein the pump housing of the LVP includes tube guides of C-shaped tubing capture structure at the periphery of the pump housing for retaining tubing of a coupled administration set beyond either side of the assembly receptacle.

18. The LVP of claim 1, wherein the assembly receptacle includes a ramp feature configured to cooperate with the free-flow protection arm of the administration set tubing assembly coupled in the assembly receptacle to prevent the free-flow protection arm from latching in the flow-allowing position.

19. A large volume pump (LVP) system that provides peristaltic pumping to supply medical infusate, comprising:
   a pump housing including an assembly receptacle;
   a drive-train assembly providing mechanical peristaltic movement, including:
      a stepper motor, located within the pump housing; and
      a camshaft assembly, driven by the stepper motor and at least partially extending into the assembly receptacle, including:
         a unitary camshaft; and
         a plurality of tube engaging members that cooperatively move according to rotation of the unitary camshaft, wherein a portion of each tube engaging member extends at least partially into the assembly receptacle;
   a controller located within the pump housing that controls operation of the stepper motor and the camshaft assembly to move the plurality of tube engaging members in a peristaltic manner;
   an administration set tubing assembly that is removably couplable with the assembly receptacle, including:
      a peristaltic tube suitable for compression by the drive-train assembly;
      a first tube coupler and a second tube coupler, each attached at opposing ends of the peristaltic tube and each having a lumen in fluidic communication with the peristaltic tube; and
      a frame coupled to the first tube coupler and the second tube coupler at spaced-apart locations, the frame configured for releasable attachment to the assembly receptacle in which the peristaltic tube is positioned for engagement with the plurality of tube engaging members; and
   a receptacle door coupled to the pump housing and including a door lever linked to a pusher, the receptacle door movable between an open position to allow access to the assembly receptacle and a closed position to block access to the assembly receptacle,
   wherein, when the administration set tubing assembly is removably coupled in the assembly receptacle and the receptacle door in the closed position, the door lever is configured to be movable to a latched position such that the pusher mechanically contacts a free-flow protection arm of the administration set tubing assembly to move the free-flow protection arm to a flow-allowing position.

20. A large volume pump (LVP) that provides peristaltic pumping to supply medical infusate, comprising:
   a housing including an assembly receptacle,
   a drive-train assembly providing mechanical peristaltic movement, including:
      a stepper motor, located within the housing; and
      a camshaft assembly, driven by the stepper motor, including:
         a unitary camshaft; and
         a plurality of tube engaging members that cooperatively move according to rotation of the unitary camshaft, wherein a portion of each tube engaging member extends at least partially into the assembly receptacle; and
   a controller located within the housing that controls operation of the stepper motor and the camshaft assembly to move the plurality of tube engaging members in a peristaltic manner,
   wherein a suspended rigid pressure plate for tube compression is located on a receptacle door that is hinged to the housing adjacent the assembly receptacle,
   wherein the assembly receptacle includes a set of horizontally-disposed guide rails located above and below the tube-engaging members to prevent vertical tube walk, and
   wherein the set of horizontally-disposed guide rails includes three projection features to define planar contact with the suspended rigid pressure plate.

21. A large volume pump (LVP) that provides peristaltic pumping to supply medical infusate, comprising:
   a housing including an assembly receptacle,
   a drive-train assembly providing mechanical peristaltic movement, including:
      a stepper motor, located within the housing; and
      a camshaft assembly, driven by the stepper motor, including:
         a unitary camshaft; and
         a plurality of tube engaging members that cooperatively move according to rotation of the unitary camshaft, wherein a portion of each tube engaging member extends at least partially into the assembly receptacle; and a controller located within the housing that controls operation of the stepper motor and the camshaft assembly to move the plurality of tube engaging members in a peristaltic manner, wherein a second internal housing is included within the housing that largely surrounds the plurality of tube-engaging members, with only ends of the plurality of tube-engaging members extending out from the second internal housing through an opening into the assembly receptacle, wherein the second internal housing is sealed at locations rearward of the tube engaging members to restrict possible fluid leakage from reaching further into the housing, and wherein weep hole apertures, that are connected to interior locations of the second internal housing, are located in the assembly receptacle at a front of the LVP pump.

* * * * *